US006586606B2

(12) United States Patent
Gerster et al.

(10) Patent No.: US 6,586,606 B2
(45) Date of Patent: Jul. 1, 2003

(54) PROCESS FOR THE PREPARATION OF 3-ARYL-BENZOFURAN-2-ONES

(75) Inventors: Michèle Gerster, Birsfelden (CH); Paul Dubs, Cham (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/899,450

(22) Filed: Jul. 5, 2001

(65) Prior Publication Data
US 2002/0115855 A1 Aug. 22, 2002

(30) Foreign Application Priority Data

Jul. 7, 2000 (EP) ............................................. 00810595

(51) Int. Cl.$^7$ ....................... C07D 407/00; C07D 307/78

(52) U.S. Cl. ........................ 549/302; 549/305; 549/467

(58) Field of Search ................................. 549/302, 305, 549/467

(56) References Cited
U.S. PATENT DOCUMENTS 5,175,312 A  * 12/1992  Dubs et al. .................. 549/307

* cited by examiner

Primary Examiner—Amelia Owens
(74) Attorney, Agent, or Firm—Kevin T. Mansfield

(57) ABSTRACT

The instant invention discloses a process for the preparation of compounds of formula I (I)

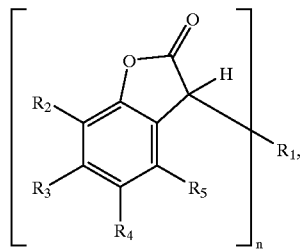

wherein the general symbols are as defined in claim 1, which process comprises hydrolyzing a compound of formula V (V)

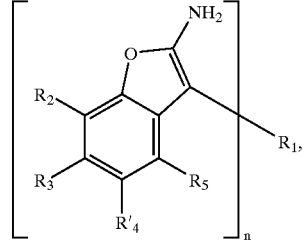

wherein the general symbols are as defined in claim 1, in an aqueous solvent in the presence of an acid. The compounds of the formula V are new and useful as stabilizers for protecting organic materials, in particular polymers and lubricants, against oxidative, thermal or light-induced degradation.

17 Claims, No Drawings

PROCESS FOR THE PREPARATION OF 3-ARYL-BENZOFURAN-2-ONES

Process for the preparation of 3-aryl-benzofuran-2-ones

The present invention relates to a novel process for the preparation of 3-aryl-benzofuran-2-ones starting from new 2-amino-benzofuranes, both of which are suitable for stabilising organic materials against oxidative, thermal or light-induced degradation.

The best processes hitherto for the preparation of 3-aryl-benzofuran-2-ones are described, for example, in U.S. Pat. No. 4,325,863; U.S. Pat. No. 5,607,624 and WO-A-99/67232.

The process disclosed in U.S. Pat. No. 4,325,863 (Example 1, column 8, lines 35–45) for the preparation of 3-phenyl-3H-benzofuran-2-ones, for example 5,7-di-tert-butyl-3-phenyl-3H-benzofuran-2-one of formula C, comprises reacting the 2,4-di-tert-butylphenol of formula A with the mandelic acid of formula B, with removal of water.

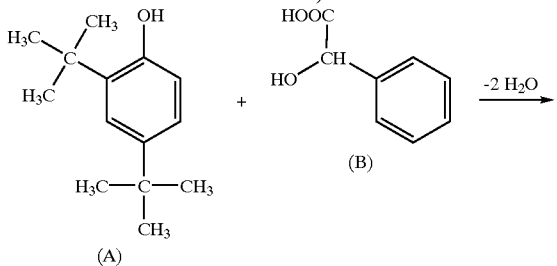

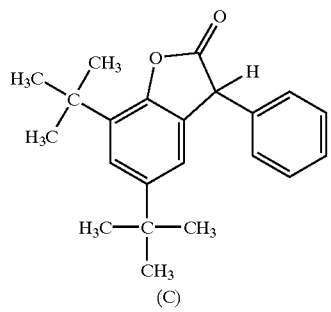

A disadvantage of that process is that it requires the use of mandelic acids substituted on the phenyl ring or heterocyclic mandelic acids. Not very many of those mandelic acids are known from the literature, however, and the known synthesis procedures for the preparation thereof are relatively complicated.

The process disclosed in U.S. Pat. No. 5,607,624 (Example 1, column 24) for the preparation of 3-phenyl-3H-benzofuran-2-ones substituted on the 3-phenyl ring, for example 5,7-di-tert-butyl-3-(2,5-dimethyl-phenyl)-3H-benzofuran-2-one of formula F, comprises reacting the 5,7-di-tert-butyl-3-hydroxy-3H-benzofuran-2-one of formula D with p-xylene of formula E, with removal of water.

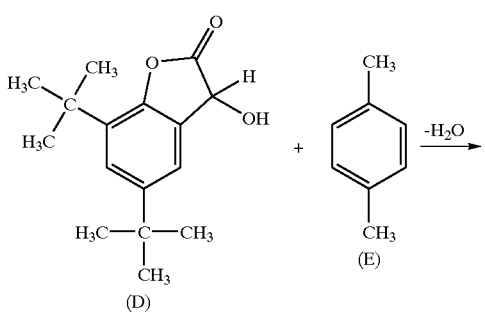

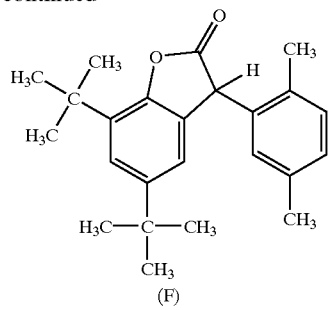

A disadvantage of that process is that, for the preparation of unsubstituted 3-phenyl-benzo-furanone derivatives, it requires the use of benzene, which is carcinogenic, instead of p-xylene.

The process disclosed in WO-A-99/67232 (Example 2, page 35) for the preparation of 3-phenyl-3 H-benzofuran-2-ones, for example 5,7-di-tert-butyl-3-phenyl-3H-benzofuran-2-one of formula C, comprises reacting a compound of formula G with carbon monoxide in the presence of a catalyst.

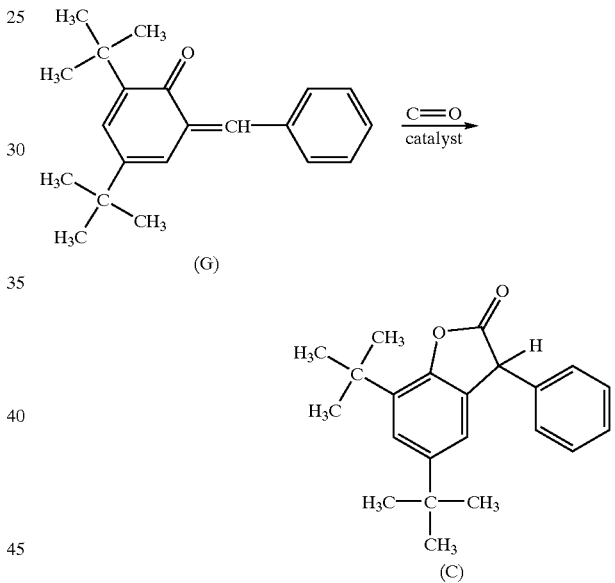

A disadvantage of that process is that it requires the use of a relatively expensive catalyst.

There is therefore still a need to find an efficient process for the preparation of 3-aryl-benzo-furan-2-ones that does not have the disadvantages mentioned above.

The present invention therefore relates to a process for the preparation of compounds of formula I

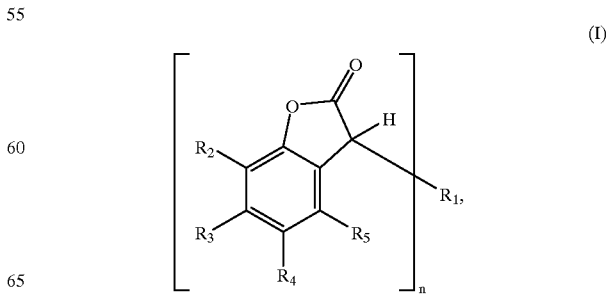

wherein, when n is 1,

R₁ is naphthyl, phenanthryl, anthryl, 5,6,7,8-tetrahydro-2-naphthyl, thienyl, benzo[b]thienyl, naphtho[2,3-b]thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyridyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$-$C_{18}$alkyl, $C_1$-$C_{18}$alkoxy, $C_1$-$C_{18}$alkylthio, di-($C_1$-$C_4$alkyl)amino, phenyl, benzyl, benzoyl or by benzoyloxy or R₁ is a radical of formula II or III

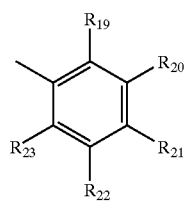
(II)

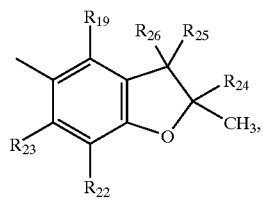
(III)

when n is 2,

R₁ is phenylene or naphthylene each unsubstituted or substituted by $C_1$-$C_4$alkyl or by fluorine; or is —R₆—X—R₇—, R₂, R₃, R₄ and R₅ are each independently of the others hydrogen, fluorine, hydroxy, $C_1$-$C_{25}$-alkyl, $C_7$-$C_9$phenylalkyl, unsubstituted or $C_1$-$C_4$alkyl-substituted phenyl, unsubstituted or $C_1$-$C_4$alkyl-substituted $C_5$-$C_8$cycloalkyl; $C_1$-$C_{18}$alkoxy, $C_1$-$C_{18}$alkylthio, $C_1$-$C_4$alkylamino, di-($C_1$-$C_4$alkyl)amino, $C_1$-$C_{25}$alkanoyloxy, $C_1$-$C_{25}$alkanoylamino; $C_3$-$C_{25}$alkanoyloxy interrupted by oxygen, sulfur or by

$C_6$-$C_9$cycloalkylcarbonyloxy, benzoyloxy or $C_1$-$C_{12}$alkyl-substituted benzoyloxy, or furthermore the radicals R₂ and R₃ or the radicals R₃ and R₄ or the radicals R₄ and R₅, together with the carbon atoms to which they are bonded, form a benzo ring, R₄ is additionally —(CH₂)$_p$—COR₉ or —(CH₂)$_q$OH or, when R₃ and R₅ are hydrogen, R₄ is additionally a radical of formula IV

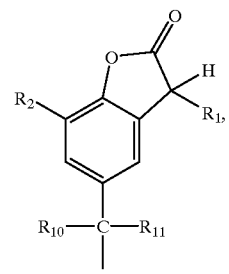
(IV)

wherein R₁ is as defined above for the case where n=1,

R₆ and R₇ are each independently of the other phenylene or naphthylene each unsubstituted or substituted by $C_1$-$C_4$alkyl, R₈ is $C_1$-$C_8$alkyl, R₉ is hydroxy,

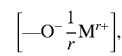

$C_1$-$C_{18}$alkoxy or

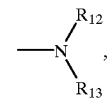

R₁₀ and R₁₁ are each independently of the other hydrogen, CF₃, $C_1$-$C_{12}$alkyl or phenyl, or R₁₀ and R₁₁, together with the carbon atom to which they are bonded, form a $C_5$-$C_8$cycloalkylidene ring unsubstituted or substituted by from 1 to 3 $C_1$-$C_4$alkyl groups;

R₁₂ and R₁₃ are each independently of the other hydrogen or $C_1$-$C_{18}$alkyl, R₁₄ is hydrogen or $C_1$-$C_{18}$alkyl, R₁₉, R₂₀, R₂₁, R₂₂ and R₂₃ are each independently of the others hydrogen, halogen, fluoro-substituted $C_1$-$C_{12}$alkyl; —CN,

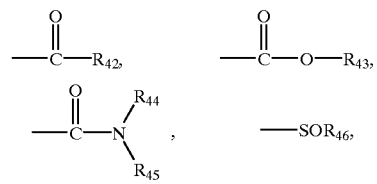

—SO₂R₄₆, SO₃R₄₆, hydroxy, $C_1$-$C_{25}$alkyl; $C_2$-$C_{25}$alkyl interrupted by oxygen, sulfur or by

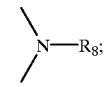

$C_1$-$C_{25}$alkoxy; $C_2$-$C_{25}$alkoxy interrupted by oxygen, sulfur or by

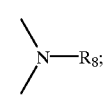

$C_1$–$C_{25}$alkylthio, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; di($C_1$–$C_4$alkyl) amino, $C_1$–$C_{25}$alkanoyl; $C_3$–$C_{25}$alkanoyl interrupted by oxygen, sulfur or by

$C_1$–$C_{25}$alkanoyloxy; $C_3$–$C_{25}$alkanoyloxy interrupted by oxygen, sulfur or by

$C_1$–$C_{25}$alkanoylamino, $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

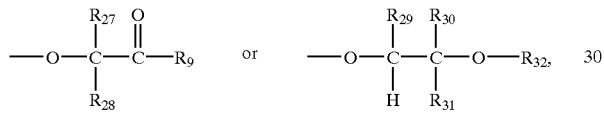

$R_{24}$ is hydrogen, $C_1$–$C_4$alkyl, or unsubstituted or $C_1$–$C_4$alkyl-substituted phenyl, $R_{25}$ and $R_{26}$ are hydrogen, $C_1$–$C_4$alkyl or phenyl, with the proviso that at least one of the radicals $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl; $C_2$–$C_{25}$alkyl interrupted by oxygen, sulfur or by

$C_7$–$C_9$phenylalkyl unsubstituted or substituted on the phenyl radical by from 1 to 3 $C_1$–$C_4$alkyl groups; or $C_7$–$C_{25}$phenylalkyl interrupted by oxygen, sulfur or by

and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl; $C_3$–$C_{25}$alkanoyl interrupted by oxygen, sulfur or by

$C_2$–$C_{25}$alkanoyl substituted by a di($C_1$–$C_6$alkyl) phosphonate group; $C_6$–$C_9$-cycloalkylcarbonyl, thenoyl, furoyl, benzoyl or $C_1$–$C_{12}$alkyl-substituted benzoyl;

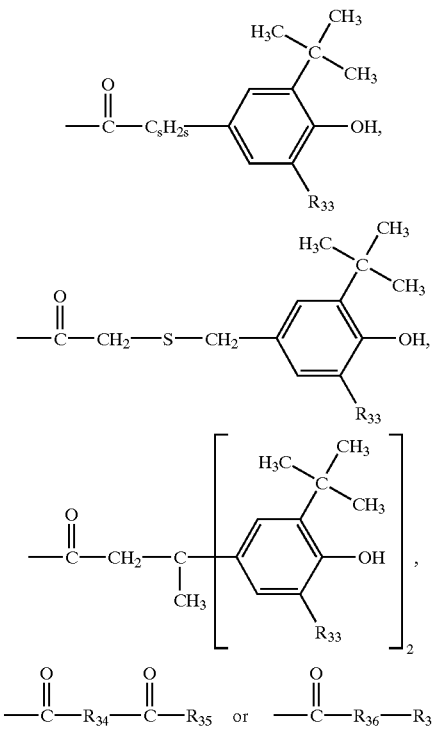

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

$C_2$–$C_{20}$alkylidene, $C_7$–$C_{20}$phenylalkylidene, $C_5$–$C_8$cycloalkylene, $C_7$–$C_8$bicyclo-alkylene, unsubstituted or $C_1$–$C_4$alkyl-substituted phenylene,

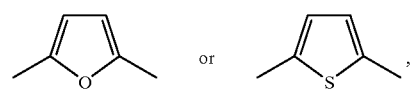

$R_{35}$ is hydroxy, $\left[ -O^- \dfrac{1}{r} M^{r+} \right]$, $C_1$–$C_{18}$alkoxy or

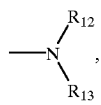

$R_{36}$ is oxygen, —NH— or

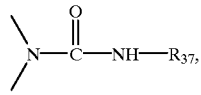

$R_{37}$ is $C_1$–$C_{18}$alkyl or phenyl,
$R_{42}$ is hydrogen, hydroxy,

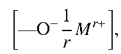

$C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

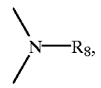

$R_{43}$ is $C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

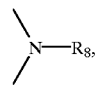

$R_{44}$ and $R_{45}$ are each independently of one another hydrogen, $C_1$–$C_{25}$alkyl, hydroxyl-substituted $C_2$–$C_{24}$alkyl; $C_3$–$C_{25}$alkyl which is interrupted by oxygen, sulfur or

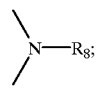

phenylalkyl which is unsubstituted or is substituted on the phenyl ring by $C_1$–$C_4$alkyl; or $C_3$–$C_{24}$alkenyl; or $R_{44}$ and $R_{45}$, together with the nitrogen atom to which they are attached, form a 5-, 6- or 7-membered heterocyclic ring which is unsubstituted or is substituted by $C_1$–$C_4$alkyl or is interrupted by oxygen, sulfur or

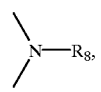

$R_{46}$ is hydrogen or $C_1$–$C_{25}$alkyl,
M is an r-valent metal cation,
X is a direct bond, oxygen, sulfur or —$NR_{14}$—,
n is 1 or 2,
p is 0, 1 or 2,
q is 1, 2, 3, 4, 5 or 6,
r is 1, 2 or 3, and
s is 0, 1 or 2,
which process comprises hydrolyzing a compound of formula V

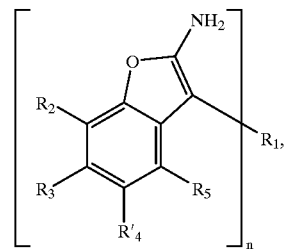

wherein
$R_1$ and n are as defined above,
$R_2$, $R_3$, $R'_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$-cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R'_4$ or the radicals $R'_4$ and $R_5$, together with the carbon atoms to which they are bonded, form a benzo ring, $R'_4$ is additionally —$(CH_2)p$—$COR_9$ or —$(CH_2)_qOH$ or, when $R_3$ and $R_5$ are hydrogen, $R'_4$ is additionally a radical of formula VI

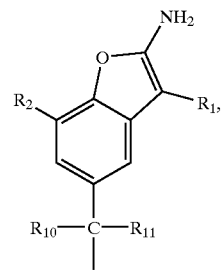

wherein $R_1$ is as defined above for the case where n=1, in an aqueous solvent in the presence of an acid.

Alkanoyl having up to 25 carbon atoms is a branched or unbranched radical, for example formyl, acetyl, propionyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, icosanoyl or docosanoyl. Alkanoyl has preferably from 2 to 18, especially from 2 to 12, e.g. from 2 to 6, carbon atoms. Special preference is given to acetyl.

$C_2$–$C_{25}$Alkanoyl substituted by a di($C_1$–$C_6$alkyl) phosphonate group is, for example, $(CH_3CH_2O)_2POCH_2CO$—, $(CH_3O)_2POCH_2CO$—, $(CH_3CH_2CH_2CH_2O)_2$ $POCH_2CO$—, $(CH_3CH_2O)_2POCH_2CH_2CO$—, $(CH_3O)_2POCH_2CH_2CO$—, $(CH_3CH_2CH_2CH_2O)_2POCH_2CH_2CO$—, $(CH_3CH_2O)_2PO(CH_2)_4CO$—, $(CH_3CH_2O)_2PO(CH_2)_8CO$— or $(CH_3CH_2O)_2PO(CH_2)_{17}CO$—.

Alkanoyloxy having up to 25 carbon atoms is a branched or unbranched radical, for example formyloxy, acetoxy, propionyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, icosanoyloxy or docosanoyloxy. Preference is given to alkanoyloxy having from 2 to 18, especially from 2 to 12, e.g. from 2 to 6, carbon atoms. Special preference is given to acetoxy.

$C_3$–$C_{25}$Alkenoyloxy interrupted by oxygen, sulfur or by

is, for example, $CH_3OCH_2CH_2CH=CHCOO$— or $CH_3OCH_2CH_2OCH=CHCOO$—.

$C_3$–$C_{25}$Alkanoyl interrupted by oxygen, sulfur or by

is, for example, $CH_3$—O—$CH_2CO$—, $CH_3$—S—$CH_2CO$—, $CH_3$—$N(CH_3)$—$CH_2CO$—, $CH_3$—O—$CH_2CH_2$—O—$CH_2CO$—, $CH_3$—(O—$CH_2CH_2$—)$_2$O—$CH_2CO$—, $CH_3$—(O—$CH_2CH_2$—)$_3$O—$CH_2CO$— or $CH_3$—(O—$CH_2CH_2$—)$_4$O—$CH_2CO$—.

$C_3$–$C_{25}$Alkanoyloxy interrupted by oxygen, sulfur or by

is, for example, $CH_3$—O—$CH_2COO$—, $CH_3$—S—$CH_2COO$—, $CH_3$—$N(CH_3)$—$CH_2COO$—, $CH_3$—O—$CH_2CH_2$—O—$CH_2COO$—, $CH_3$—(O—$CH_2CH_2$—)$_2$O—$CH_2COO$—, $CH_3$—(O—$CH_2CH_2$—)$_3$O—$CH_2COO$— or $CH_3$—(O—$CH_2CH_2$—)$_4$O—$CH_2COO$—.

$C_6$–$C_9$Cycloalkylcarbonyl is, for example, cyclopentylcarbonyl, cyclohexylcarbonyl, cycloheptylcarbonyl or cyclooctylcarbonyl. Preference is given to cyclohexylcarbonyl.

$C_6$–$C_9$Cycloalkylcarbonyloxy is, for example, cyclopentylcarbonyloxy, cyclohexylcarbonyloxy, cycloheptylcarbonyloxy or cyclooctylcarbonyloxy. Preference is given to cyclohexylcarbonyloxy.

$C_1$–$C_{12}$Alkyl-substituted benzoyl, which carries preferably from 1 to 3, especially 1 or 2, alkyl groups, is, for example, o-, m- or p-methylbenzoyl, 2,3-dimethylbenzoyl, 2,4-dimethyl-benzoyl, 2,5-dimethylbenzoyl, 2,6-dimethylbenzoyl, 3,4-dimethylbenzoyl, 3,5-dimethylbenzoyl, 2-methyl-6-ethylbenzoyl, 4-tert-butylbenzoyl, 2-ethylbenzoyl, 2,4,6-trimethylbenzoyl, 2,6-dimethyl-4-tert-butylbenzoyl or 3,5-di-tert-butylbenzoyl. Preferred substituents are $C_1$–$C_8$-alkyl, especially $C_1$–$C_4$alkyl.

$C_1$–$C_{12}$Alkyl-substituted benzoyloxy, which carries preferably from 1 to 3, especially 1 or 2, alkyl groups, is, for example, o-, m- or p-methylbenzoyloxy, 2,3-dimethylbenzoyloxy, 2,4-di-methylbenzoyloxy, 2,5-dimethylbenzoyloxy, 2,6-dimethylbenzoyloxy, 3,4-dimethylbenzoyloxy, 3,5-dimethylbenzoyloxy, 2-methyl-6-ethylbenzoyloxy, 4-tert-butylbenzoyloxy, 2-ethylbenzoyloxy, 2,4,6-trimethylbenzoyloxy, 2,6-dimethyl-4-tert-butylbenzoyloxy or 3,5-di-tert-butylbenzoyloxy. Preferred substituents are $C_1$–$C_8$alkyl, especially $C_1$–$C_4$alkyl.

Alkyl having up to 25 carbon atoms is a branched or unbranched radical, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl. One of the preferred definitions for $R_2$ and $R_4$ is, for example, $C_1$–$C_{18}$alkyl. An especially preferred definition for $R_4$ is $C_1$–$C_4$alkyl.

$C_2$–$C_{25}$Alkyl interrupted by oxygen, sulfur or by

is, for example, $CH_3$—O—$CH_2$—, $CH_3$—S—$CH_2$—, $CH_3$—$N(CH_3)$—$CH_2$—, $CH_3$—O—$CH_2CH_2$—O—$CH_2$—, $CH_3$—(O—$CH_2CH_2$—)$_2$O—$CH_2$—, $CH_3$—(O—$CH_2CH_2$—)$_3$O—$CH_2$— or $CH_3$—(O—$CH_2CH_2$—)$_4$O—$CH_2$—.

$C_7$–$C_9$Phenylalkyl is, for example, benzyl, α-methylbenzyl, α,α-dimethylbenzyl or 2-phenyl-ethyl. Preference is given to benzyl and α,α-dimethylbenzyl.

$C_7$–$C_9$Phenylalkyl unsubstituted or substituted on the phenyl radical by from 1 to 3 $C_1$–$C_4$alkyl groups is, for example, benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tertbutylbenzyl. Preference is given to benzyl.

$C_7$–$C_{25}$Phenylalkyl interrupted by oxygen, sulfur or by

and unsubstituted or substituted on the phenyl radical by from 1 to 3 $C_1$–$C_4$alkyl groups is a branched or unbranched radical, for example phenoxymethyl, 2-methyl-phenoxymethyl, 3-methyl-phenoxymethyl, 4-methyl-phenoxymethyl, 2,4-dimethyl-phenoxymethyl, 2,3-dimethyl-phenoxymethyl, phenylthiomethyl, N-methyl-N-phenyl-aminomethyl, N-ethyl-N-phenyl-aminomethyl, 4-tert-butyl-phenoxymethyl, 4-tert-butyl-phenoxyethoxymethyl, 2,4-di-tert-butyl-phenoxymethyl, 2,4-di-tert-butyl-phenoxyethoxymethyl, phenoxyethoxyethoxyethoxymethyl, benzyloxym ethyl, benzyloxyethoxymethyl, N-benzyl-N-ethyl-aminomethyl or N-benzyl-N-isopropyl-aminomethyl.

$C_7$–$C_9$Phenylalkoxy is, for example, benzyloxy, α-methylbenzyloxy, α,α-dimethylbenzyloxy or 2-phenylethoxy. Preference is given to benzyloxy.

$C_1$–$C_4$Alkyl-substituted phenyl, which contains preferably from 1 to 3, especially 1 or 2, alkyl groups, is, for example, o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

$C_1$–$C_4$Alkyl-substituted phenoxy, which contains preferably from 1 to 3, especially 1 or 2, alkyl groups, is, for example, o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

Unsubstituted or $C_1$–$C_4$alkyl-substituted $C_5$–$C_8$cycloalkyl is, for example, cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Preference is given to cyclohexyl and tert-butylcyclohexyl.

Unsubstituted or $C_1$–$C_4$alkyl-substituted $C_5$–$C_8$cycloalkoxy is, for example, cyclopentyloxy, methylcyclopentyloxy, dimethylcyclopentyloxy, cyclohexyloxy, methylcyclohexyloxy, dimethylcyclohexyloxy, trimethylcyclohexyloxy, tert-butylcyclohexyloxy, cycloheptyloxy or cyclooctyloxy. Preference is given to cyclohexyloxy and tert-butylcyclohexyloxy.

Alkoxy having up to 25 carbon atoms is a branched or unbranched radical, for example methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy. Preference is given to alkoxy having from 1 to 12, especially from 1 to 8, e.g. from 1 to 6, carbon atoms.

$C_2$–$C_{25}$Alkoxy interrupted by oxygen, sulfur or by

is, for example, $CH_3$—O—$CH_2CH_2$O—, $CH_3$—S—$CH_2CH_2$O—, $CH_3$—N($CH_3$)—$CH_2CH_2$O—, $CH_3$—O—$CH_2CH_2$—O—$CH_2CH_2$O—, $CH_3$—(O—$CH_2CH_2$—)$_2$O—$CH_2CH_2$O—, $CH_3$—(O—$CH_2CH_2$—)$_3$O—$CH_2CH_2$O— or $CH_3$—(O—$CH_2CH_2$—)$_4$O—$CH_2CH_2$O—.

Alkylthio having up to 25 carbon atoms is a branched or unbranched radical, for example methylthio, ethylthio, propylthio, isopropylthio, n-butylthio, isobutylthio, pentylthio, isopentylthio, hexylthio, heptylthio, octylthio, decylthio, tetradecylthio, hexadecylthio or octadecylthio. Preference is given to alkylthio having from 1 to 12, especially from 1 to 8, e.g. from 1 to 6, carbon atoms.

Alkylamino having up to 4 carbon atoms is a branched or unbranched radical, for example methylamino, ethylamino, propylamino, isopropylamino, n-butylamino, isobutylamino or tertbutylamino.

Di($C_1$–$C_4$alkyl)amino means also that the two radicals are each independently of the other branched or unbranched, for example, dimethylamino, methylethylamino, diethylamino, methyl-n-propylamino, methylisopropylamino, methyl-n-butylamino, methylisobutylamino, ethylisopropylamino, ethyl-n-butylamino, ethylisobutylamino, ethyl-tert-butylamino, diethylamino, diisopropylamino, isopropyl-n-butylamino, isopropylisobutylamino, di-n-butylamino or di-isobutylamino.

Alkanoylamino having up to 25 carbon atoms is a branched or unbranched radical, for example formylamino, acetylamino, propionylamino, butanoylamino, pentanoylamino, hexanoylamino, heptanoylamino, octanoylamino, nonanoylamino, decanoylamino, undecanoyl-amino, dodecanoylamino, tridecanoylamino, tetradecanoylamino, pentadecanoylamino, hexadecanoylamino, heptadecanoylamino, octadecanoylamino, icosanoylamino or docosanoylamino. Preference is given to alkanoylamino having from 2 to 18, especially from 2 to 12, e.g. from 2 to 6, carbon atoms.

$C_1$–$C_{18}$Alkylene is a branched or unbranched radical, for example methylene, ethylene, propylene, trimethylene, tetramethylene, pentamethylene, hexamethylene, heptamethylene, octamethylene, decamethylene, dodecamethylene or octadecamethylene. Preference is given to $C_1$–$C_{12}$alkylene, especially $C_1$–$C_8$alkylene. An especially preferred definition for $R_{56}$ is $C_2$–$C_8$alkylene, especially $C_4$–$C_8$alkylene, for example tetramethylene or pentamethylene.

$C_2$–$C_{18}$Alkylene interrupted by oxygen, sulfur or by

is, for example, —$CH_2$—O—$CH_2$—, —$CH_2$—S—$CH_2$—, —$CH_2$—N($CH_3$)—$CH_2$—, —$CH_2$—O—$CH_2CH_2$—O—$CH_2$—, —$CH_2$—(O—$CH_2CH_2$—)$_2$O—$CH_2$—, —$CH_2$—(O—$CH_2CH_2$—)$_3$O—$CH_2$—, —$CH_2$—(O—$CH_2CH_2$—)$_4$O—$CH_2$— or —$CH_2CH_2$—S—$CH_2CH_2$—, Alkylidene having from 2 to 20 carbon atoms is, for example, ethylidene, propylidene, butylidene, pentylidene, 4-methylpentylidene, heptylidene, nonylidene, tridecylidene, nonadecylidene, 1-methylethylidene, 1-ethylpropylidene or 1-ethylpentylidene. Preference is given to $C_2$–$C_8$alkylidene.

Phenylalkylidene having from 7 to 20 carbon atoms is, for example, benzylidene, 2-phenyl-ethylidene or 1-phenyl-2-hexylidene. Preference is given to $C_7$–$C_9$phenylalkylidene.

$C_5$–$C_8$Cycloalkylene is a saturated hydrocarbon group having two free valences and at least one ring unit and is, for example, cyclopentylene, cyclohexylene, cycloheptylene or cyclooctylene. Preference is given to cyclohexylene.

$C_7$–$C_8$Bicycloalkylene is, for example, bicycloheptylene or bicyclooctylene.

Phenylene or naphthylene each unsubstituted or substituted by $C_1$–$C_4$alkyl is, for example, 1,2-, 1,3- or 1,4-phenylene or 1,2-, 1,3-, 1,4-, 1,6-, 1,7-, 2,6- or 2,7-naphthylene. Preference is given to 1,4-phenylene.

A $C_5$–$C_8$cycloalkylidene ring substituted by $C_1$–$C_4$alkyl, which contains preferably from 1 to 3, especially 1 or 2, branched or unbranched alkyl group radicals, is, for example, cyclopentylidene, methylcyclopentylidene, dimethylcyclopentylidene, cyclohexylidene, methylcyclohexylidene, dimethylcyclohexylidene, trimethylcyclohexylidene, tert-butylcyclohexylidene, cycloheptylidene or cyclooctylidene. Preference is given to cyclohexylidene and tert-butylcyclo-hexylidene.

A mono-, di- or tri-valent metal cation is preferably an alkali metal cation, alkaline earth metal cation or aluminium cation, for example $Na^+$, $K^+$, $Mg^{++}$, $Ca^{++}$ or $Al^{+++}$.

Dendrimeric, oligomeric or polymeric $C_4$–$C_{100}$hydrocarbon radicals are, for example, those such as are disclosed by R. Mülhaupt et al. in Angew. Chem., Int. Ed. 32 (9), 1306 (1993).

Halogen is, for example, chlorine, bromine or iodine. Preference is given to chlorine and bromine.

Fluoro-substituted $C_1$–$C_{12}$alkyl is a branched or unbranched radical, for example fluoromethyl, difluoromethyl, trifluoromethyl or pentafluoroethyl. Trifluoromethyl is preferred.

Hydroxyl-substituted $C_2$–$C_{24}$alkyl is a branched or unbranched radical which contains preferably 1 to 3, in particular 1 or 2, hydroxyl groups, such as, for example, hydroxyethyl, 3-hydroxypropyl, 2-hydroxypropyl, 4-hydroxybutyl, 3-hydroxybutyl, 2-hydroxybutyl, 5-hydroxypentyl, 4-hydroxypentyl, 3-hydroxypentyl, 2-hydroxypentyl, 6-hydroxyhexyl, 5-hydroxyhexyl, 4-hydroxyhexyl, 3-hydroxyhexyl, 2-hydroxyhexyl, 7-hydroxyheptyl, 6-hydroxyheptyl, 5-hydroxyheptyl, 4-hydroxyheptyl, 3-hydroxyheptyl, 2-hydroxyheptyl, 8-hydroxyoctyl, 7-hydroxyoctyl, 6-hydroxyoctyl, 5-hydroxyoctyl, 4-hydroxyoctyl, 3-hydroxyoctyl, 2-hydroxyoctyl, 9-hydroxynonyl, 10-hydroxydecyl, 11-hydroxyundecyl, 12-hydroxydodecyl, 13-hydroxytridecyl, 14-hydroxytetradecyl, 15-hydroxypentadecyl, 16-hydroxyhexadecyl, 17-hydroxyheptadecyl, 18-hydroxyoctadecyl, 20-hydroxyeicosyl or 22-hydroxydocosyl. A preferred definition of $R_{44}$ and $R_{45}$ is hydroxyl-substituted $C_2$–$C_{20}$alkyl, especially hydroxyl-substituted $C_2$–$C_{18}$alkyl, for example hydroxyl-substituted $C_2$–$C_{14}$alkyl. A particularly preferred definition of $R_{44}$ and $R_{45}$ is hydroxyl-substituted $C_2$–$C_{12}$alkyl, especially hydroxyl-substituted $C_2$–$C_8$alkyl, for example hydroxyl-substituted $C_2$–$C_4$alkyl, such as 2-hydroxyethyl, for example.

Where $R_{44}$ and $R_{45}$ together with the nitrogen atom to which they are attached, form a 5-, 6- or 7-membered heterocyclic ring which is unsubstituted or is substituted by $C_1$–$C_4$alkyl or is interrupted by oxygen, sulfur or

this denotes, for example, the following radicals:

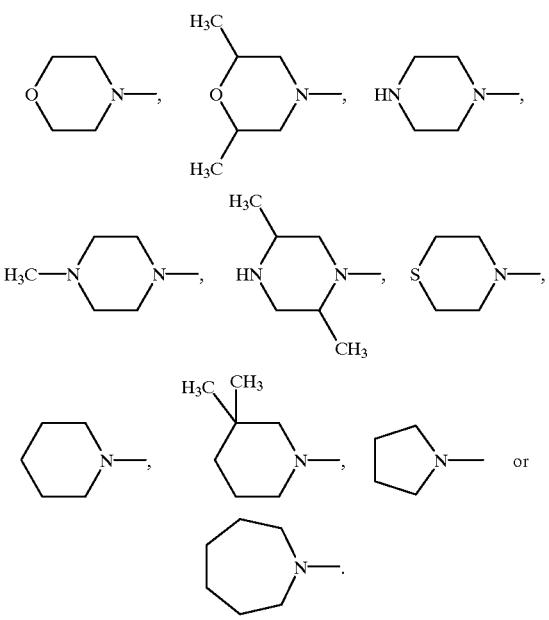

$R_{44}$ and $R_{45}$ or $R_{27}$ preferably form, with the nitrogen atom to which they are attached, a 6-membered heterocyclic ring interrupted by oxygen, such as, for example,

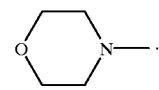

Of interest is a process for the preparation of compounds of formula I wherein, when n is 2, $R_1$ is phenylene or —$R_6$—X—$R_7$—, $R_6$ and $R_7$ are phenylene, X is oxygen or —$NR_{14}$—, and $R_{14}$ is $C_1$–$C_4$alkyl.

Likewise of interest is a process for the preparation of compounds of formula I wherein $R_{19}$, $R_{20}$, $R_{21}$, $R_{22}$ and $R_{23}$ are each independently of the others hydrogen, chloro, bromo, fluoro-substituted $C_1$–$C_{12}$alkyl; —CN,

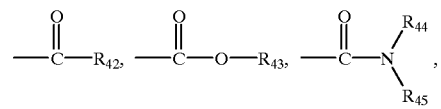

—$SOR_{46}$, —$SO_2R_{46}$, $SO_3R_{46}$, hydroxy, $C_1$–$C_{18}$alkyl; $C_2$–$C_{18}$alkyl interrupted by oxygen or by sulfur; $C_1$–$C_{18}$alkoxy; $C_2$–$C_{18}$alkoxy interrupted by oxygen or by sulfur; $C_1$–$C_{18}$alkylthio, $C_7$–$C_9$phenylalkyl, $C_7$–$C_9$phenylalkoxy, unsubstituted or $C_1$–$C_4$alkyl substituted phenyl; phenoxy, cyclohexyl, $C_5$–$C_8$cycloalkoxy, di($C_1$–$C_4$alkyl)amino, $C_1$–$C_{12}$alkanoyl; $C_3$–$C_{12}$alkanoyl interrupted by oxygen or by sulfur; $C_1$–$C_{12}$alkanoyloxy; $C_3$–$C_{12}$alkanoyloxy interrupted by oxygen or by sulfur; $C_1$–$C_{12}$alkanoylamino, cyclohexylcarbonyl, cyclohexylcarbonyloxy, benzoyl or $C_1$–$C_4$alkyl-substituted benzoyl; benzoyloxy or $C_1$–$C_4$alkyl-substituted benzoyloxy;

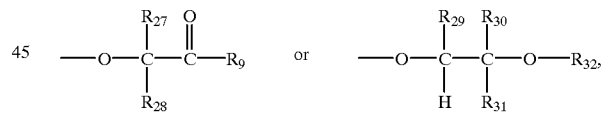

$R_{24}$ is hydrogen or $C_1$–$C_4$alkyl, $R_{25}$ and $R_{26}$ are hydrogen or $C_1$–$C_4$alkyl, with the proviso that at least one of the radicals $R_{25}$ and $R_{26}$ is hydrogen, $R_{27}$ and $R_{28}$ are each independently of the other hydrogen or $C_1$–$C_4$alkyl, $R_{29}$ is hydrogen, $R_{30}$ is hydrogen, phenyl, $C_1$–$C_{18}$alkyl; $C_2$–$C_{18}$alkyl interrupted by oxygen or by sulfur; $C_7$–$C_9$-phenylalkyl; or $C_7$–$C_{18}$phenylalkyl interrupted by oxygen or by sulfur and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl; $C_3$–$C_{12}$alkanoyl interrupted by oxygen or by sulfur; $C_2$–$C_{12}$-alkanoyl substituted by a di($C_1$–$C_6$alkyl) phosphonate group; $C_6$–$C_9$cycloalkylcarbonyl, benzoyl,

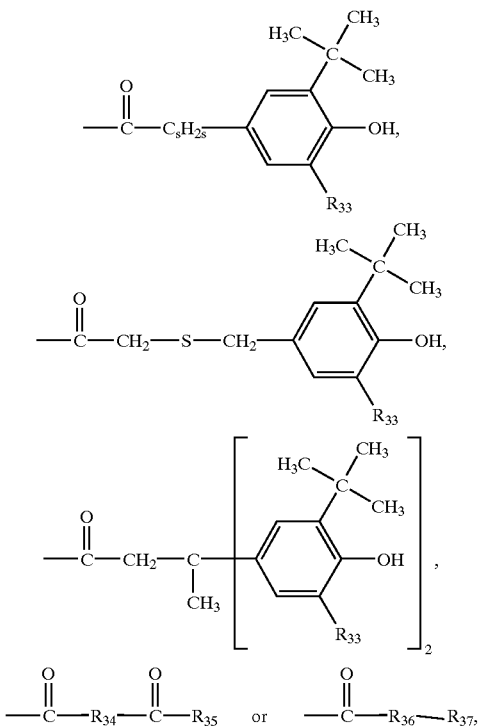

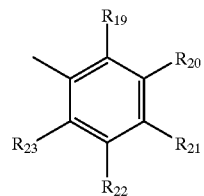

$R_1$ is naphthyl, phenanthryl, thienyl, pyridyl, dibenzofuryl, unsubstituted or $C_1$–$C_4$alkyl-substituted carbazolyl; or fluorenyl, or $R_1$ is a radical of formula II when n is 2,
$R_1$ is phenylene or naphthylene;
$R_{19}$, $R_{20}$, $R_{21}$, $R_{22}$ and $R_{23}$ are each independently of the others hydrogen, chloro, bromo, fluoro-substituted $C_1$–$C_8$alkyl; —CN,

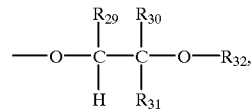

hydroxy, $C_1$–$C_{18}$alkyl, $C_1$–$C_{18}$alkoxy, $C_1$–$C_{18}$alkylthio, phenyl, benzoyl, benzoyloxy or $R_{33}$ is hydrogen or $C_1$–$C_4$alkyl, $R_{34}$ is $C_1$–$C_2$alkylene, $C_2$–$C_8$alkylidene, $C_7$–$C_{12}$phenylalkylidene, $C_5$–$C_8$cycloalkylene or phenylene, $R_{35}$ is hydroxy, $$\left[-O^- \tfrac{1}{r} M^{r+}\right]$$

or $C_1$–$C_{18}$alkoxy, $R_{36}$ is oxygen or —NH—, $R_{37}$ is $C_1$–$C_8$alkyl or phenyl, $R_{42}$ is hydrogen, hydroxy, $C_1$–$C_{18}$alkyl, $C_7$–$C_9$phenylalkyl, unsubstituted or $C_1$–$C_4$alkyl-substituted phenyl; $C_5$–$C_8$cycloalkyl; or $C_3$–$C_{25}$alkyl which is interrupted by oxygen or sulfur, $R_{43}$ is $C_1$–$C_{18}$alkyl, $C_7$–$C_9$phenylalkyl, unsubstituted or Cl-$C_4$alkyl-substituted phenyl; $C_5$–$C_8$cycloalkyl; or $C_3$–$C_{18}$alkyl which is interrupted by oxygen or sulfur, $R_{44}$ and $R_{45}$ are each independently of one another hydrogen, $C_1$–$C_{18}$alkyl, hydroxyl-substituted $C_2$–$C_{18}$alkyl; $C_3$–$C_{18}$alkyl which is interrupted by oxygen or sulfur; $C_7$–$C_9$-phenylalkyl, or $C_3$–$C_{18}$alkenyl; or $R_{44}$ and $R_{45}$, together with the nitrogen atom to which they are attached, form a 6-membered heterocyclic ring, $R_{46}$ is $C_1$–$C_{18}$alkyl, and s is 1 or 2.

Of special interest is a process for the preparation of compounds of formula I wherein, when n is 1, $R_{29}$ is hydrogen,
$R_{30}$ is hydrogen, phenyl or $C_1$–$C_{18}$alkyl,
$R_{31}$ is hydrogen or $C_1$–$C_4$alkyl,
$R_{32}$ is hydrogen, $C_1$–$C_{12}$alkanoyl or benzoyl, and
$R_{43}$ is $C_1$–$C_{18}$alkyl, benzyl, phenyl; cyclohexyl; or $C_3$–$C_{12}$alkyl which is interrupted by oxygen, and
$R_{44}$ and $R_{45}$ are each independently of one another hydrogen, $C_1$–$C_{14}$alkyl, hydroxyl-substituted $C_2$–$C_{14}$alkyl; $C_3$–$C_{12}$alkyl which is interrupted by oxygen; benzyl or $C_3$–$C_{12}$alkenyl.

Likewise of special interest is a process for the preparation of compounds of formula I wherein
$R_{19}$ is hydrogen, hydroxy, bromo, trifluoromethyl, $C_1$–$C_4$alkyl or $C_1$–$C_4$alkoxy,
$R_{20}$ is hydrogen, bromo, trifluoromethyl, $C_1$–$C_4$alkyl or $C_1$–$C_4$alkoxy,
$R_{21}$ is hydrogen, bromo, trifluoromethyl, $C_1$–$C_4$alkyl, $C_1$–$C_4$alkoxy, $C_1$–$C_4$alkylthio,
$R_{22}$ is hydrogen, bromo, trifluoromethyl, $C_1$–$C_4$alkyl or $C_1$–$C_4$alkoxy, and
$R_{23}$ is hydrogen, hydroxy, bromo, trifluoromethyl, $C_1$–$C_4$alkyl or $C_1$–$C_4$alkoxy.

Of special interest is, more especially, a process for the preparation of compounds of formula I wherein
$R_2$, $R_3$, $R_4$ and $R_5$ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di-($C_1$–$C_4$alkyl)amino, $C_1$–$C_{18}$alkanoyloxy, $C_1$–$C_{18}$alkanoylamino; $C_3$–$C_{18}$alkanoyloxy interrupted by oxygen, sulfur or by

$C_6$–$C_9$cycloalkylcarbonyloxy, benzoyloxy or $C_1$–$C_8$alkyl-substituted benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —$(CH_2)_p$—$COR_9$ or —$(CH_2)_q$OH or, when $R_3$ and $R_5$ are hydrogen, $R_4$ is additionally a radical of formula IV

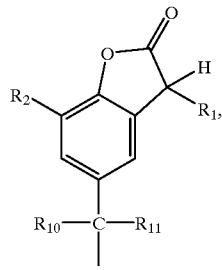

(IV)

$R_8$ is $C_1$–$C_6$alkyl,
$R_9$ is hydroxy, $C_1$–$C_{18}$alkoxy or

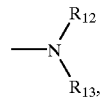

$R_{10}$ and $R_{11}$ are methyl groups or, together with the carbon atom to which they are bonded, form a $C_5$–$C_8$cycloalkylidene ring unsubstituted or substituted by from 1 to 3 $C_1$–$C_4$alkyl groups;
$R_{12}$ and $R_{13}$ are each independently of the other hydrogen or $C_1$–$C_8$alkyl, and
q is 2, 3, 4, 5 or 6.

Special preference is given to a process for the preparation of compounds of formula I wherein at least two of the radicals $R_2$, $R_3$, $R_4$ and $R_5$ are hydrogen.

Also very especially preferred is a process for the preparation of compounds of formula I wherein $R_3$ and $R_5$ are hydrogen.

Very special preference is given to a process for the preparation of compounds of formula I wherein
$R_2$, $R_3$, $R_4$ and $R_5$ are each independently of the others hydrogen, fluorine, hydroxy, $C_1$–$C_{18}$-alkyl, $C_7$–$C_9$phenylalkyl, phenyl, $C_5$–$C_8$cycloalkyl, $C_1$–$C_6$alkoxy, cyclohexylcarbonyloxy or benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —$(CH_2)_p$—$COR_9$, or, when $R_3$ and $R_5$ are hydrogen, $R_4$ is additionally a radical of formula IV,
$R_9$ is hydroxy or $C_1$–$C_{18}$alkoxy, and
$R_{10}$ and $R_{11}$ are methyl groups or, together with the carbon atom to which they are bonded, form a $C_5$–$C_8$cycloalkylidene ring.

Of preferential interest is a process for the preparation of compounds of formula I wherein
$R_2$ is $C_1$–$C_{18}$alkyl or cyclohexyl,
$R_3$ is hydrogen,
$R_4$ is $C_1$–$C_4$alkyl, cyclohexyl, —$(CH_2)_p$—$COR_9$ or a radical of formula IV,
$R_5$ is hydrogen,
$R_9$ is $C_1$–$C_4$alkyl,
$R_{10}$ and $R_{11}$, together with the carbon atom to which they are bonded, form a cyclohexylidene ring, and
p is 2.

Preferred reaction conditions for the process according to the invention are as follows:

The reaction may be carried out at an elevated temperature, especially at temperatures of from 20 to 200° C., especially of from 20 to 150° C., e.g. from 20 to 80° C., in an aqueous solvent, optionally under slight pressure.

Preferred aqueous solvents are for example aqueous alcohols, aqueous dimethyl sulfoxide, aqueous sulfolane, aqueous dimethyl formamide, aqueous tetrahydrofurane or aqueous dioxane. Aqueous alcohols are especially preferred.

Especially preferred aqueous alcohols are $C_1$–$C_{12}$alcohols or $C_1$–$C_{12}$alcohols interrupted by oxygen. Examples of such alcohols methanol, ethanol, n-propanol, iso-propanol, n-butanol, iso-butanol, tert-butanol, n-pentanol, glycol, glycerol, ethylene glycol or diethylene glycol.

Preferred acids are for example hydrochloric acid, hydrobromic acid, sulfuric acid, nitric acid phosphoric acid, sulfonic acids or carboxylic acids. Hydrochloric acid is especially preferred.

Preferred sulfonic acids are for example methane sulfonic acid or p-toluene sulfonic acid. Preferred carboxylic acids are for example formic acid, acetic acid, propionic acid, trifluoroacetic acid, oxalic acid or phthalic acid.

The acid is preferably used in at least an equal molar amount in respect to the compound of the formula V. Preferably, the molar ratio between the acid and the compound of the formula V is 4:1 to 1:1; especially 2:1 to 1:1, for example 1.3:1 to 1:1.

The starting compounds of formula V are new and can be prepared for example by the following new process.

The present invention therefore relates also to a preferred process for the preparation of the starting compounds of formula V

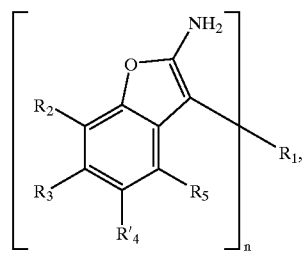

(V)

wherein the general symbols are as defined above, comprises converting a compound of formula VII

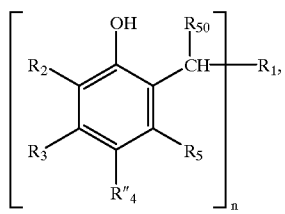

(VII)

wherein $R_1$ and n are as defined above,
$R_2$, $R_3$, $R''_4$ and $R_5$ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R''_4$ or the radicals $R''_4$ and $R_5$, together with the carbon atoms to which they are bonded, form a benzo ring, $R''_4$ is additionally —$(CH_2)_p$—$COR_9$ or —$(CH_2)_9OH$ or, when $R_3$ and $R_5$ are hydrogen, $R''_4$ is additionally a radical of formula VIII

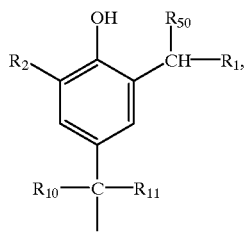

(VIII)

wherein $R_1$ is as defined above for the case where n=1, $R_2$, $R_{10}$ and $R_{11}$ are as defined above,
$R_{50}$ is —$OR_{51}$, —$SR_{52}$,

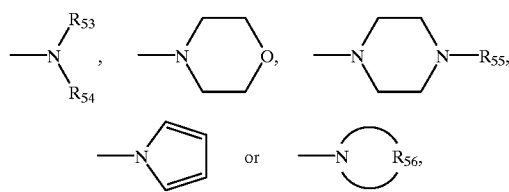

$R_{51}$ is $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$cycloalkyl; unsubstituted or $C_1$–$C_4$alkyl-substituted phenyl,
$R_{52}$ is $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$cycloalkyl; unsubstituted or $C_1$–$C_4$alkyl-substituted phenyl, $R_{53}$ and $R_{54}$ are each independently of the other hydrogen, $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$-cycloalkyl; or a dendrimeric, oligomeric or polymeric $C_4$–$C_{100}$hydrocarbon radical,
$R_{55}$ is $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$cycloalkyl; unsubstituted or $C_1$–$C_4$alkyl-substituted phenyl; or a radical of formula IX

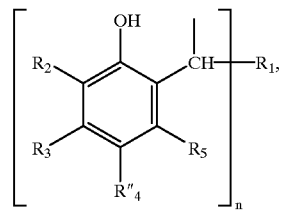

(IX)

wherein $R_1$, $R_2$, $R_3$, $R''_4$, $R_5$ and n are as defined above,
$R_{56}$ is unsubstituted or $C_1$–$C_4$alkyl-substituted $C_2$–$C_{12}$alkylene,
with an aqueous cyanide salt solution.

Preferred reaction conditions for this process are as follows:

The reaction may be carried out at an elevated temperature, especially at temperatures of from 20 to 200° C., especially of from 50 to 150° C, e.g. 80 to 130° C., in an solvent, optionally under slight pressure.

Preferred cyanide salts are alkali metal cyanide salts like for example sodium cyanide or potassium cyanide.

Preferred aqueous solvents are for example aqueous dimethyl sulfoxide, aqueous sulfolane, aqueous dimethyl formamide, aqueous tetrahydrofurane or aqueous dioxane. Aqueous sulfolane is especially preferred.

The cyanide salt is preferably used in at least an equal molar amount in respect to the compound of the formula VII. Preferably, the molar ratio between the cyanide salt and the compound of the formula VII is 20:1 to 1:1; especially 10:1 to 1:1, for example 8:1 to 1:1.

Preference is given to the process for the preparation of compounds of formula V wherein
$R_{50}$ is —$OR_{51}$, —$SR_{52}$,

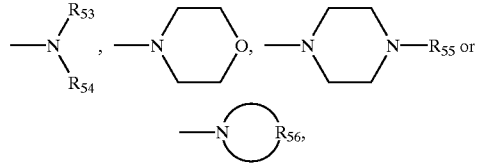

$R_{51}$ is $C_1$–$C_{12}$alkyl; $C_2$–$C_{12}$alkyl interrupted by oxygen; benzyl, $C_5$–$C_8$cycloalkyl or phenyl,
$R_{52}$ is $C_1$–$C_{12}$alkyl; $C_2$–$C_{12}$alkyl interrupted by oxygen; benzyl, $C_5$–$C_8$cycloalkyl or phenyl,
$R_{53}$ and $R_{54}$ are each independently of the other hydrogen, $C_1$–$C_{12}$alkyl; $C_2$–$C_{12}$alkyl interrupted by oxygen; benzyl, $C_5$–$C_8$cycloalkyl, or a dendrimeric or oligomeric or polymeric $C_4$–$C_{50}$hydrocarbon radical,
$R_{55}$ is $C_1$–$C_{12}$alkyl; $C_2$–$C_{12}$alkyl interrupted by oxygen; benzyl, $C_5$–$C_8$cycloalkyl, phenyl or a radical of formula IX

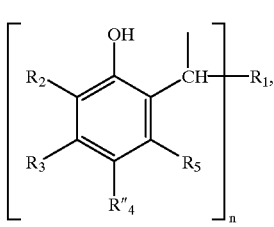

wherein $R_1$, $R_2$, $R_3$, $R''_4$, $R_5$ and n are as defined above, and $R_{56}$ is $C_2$–$C_8$alkylene.

Special preference is given to the process for the preparation of compounds of formula V wherein $R_{50}$ is

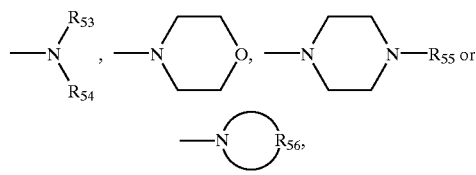

$R_{53}$ and $R_{54}$ are each independently of the other hydrogen, $C_1$–$C_{12}$alkyl, benzyl, cyclohexyl or a dendrimeric $C_4$–$C_{30}$hydrocarbon radical,
$R_{55}$ is $C_1$–$C_{12}$alkyl, benzyl, cyclohexyl, phenyl or a radical of formula IX (IX)

wherein $R_1$, $R_2$, $R_3$, $R''_4$, $R_5$ and n are as defined above, and $R_{56}$ is $C_4$–$C_8$alkylene.

Of special interest is the process for the preparation of compounds of formula V wherein $R_{50}$ is $R_{53}$ and $R_{54}$ are each independently of the other $C_1$–$C_{12}$alkyl, benzyl or a dendrimeric $C_4$–$C_{30}$hydrocarbon radical, and
$R_{56}$ is $C_4$–$C_6$alkylene.

The compounds of formula VII are known or can be obtained by methods known per se, such as those disclosed in Examples 1a, 2a and 3a of WO-A-99/67232.

The compounds of formula I can also be prepared in a so-called one-pot process, starting from the compounds of formula VII. In that process, the compounds of formula V are prepared in situ and, without being isolated, are hydrolyzed further in an aqueous solvent in the presence of an acid.

The present invention therefore relates also to a process for the preparation of compounds of formula I

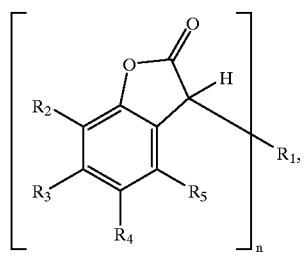

wherein the general symbols are as defined above, which process comprises converting a compound of formula VII (VII)

wherein the general symbols are as defined above, with an aqueous cyanide salt solution to form a compound of formula V (V)

wherein the general symbols are as defined above, and then, without its being isolated, hydrolyzing the compound of formula V in an aqueous solvent in the presence of an acid.

The definitions of the general symbols for the one-pot process according to the invention are the same as for the other process of the invention discussed hereinbefore.

The preferred reaction parameters for the one-pot process correspond to the preferences for the two separate steps, which have already been discussed in detail.

The invention relates also to novel compounds of formula V (V)

wherein, when n is 1,

R₁ is naphthyl, phenanthryl, anthryl, 5,6,7,8-tetrahydro-2-naphthyl, thienyl, benzo[b]thienyl, naphtho[2,3-b]thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyridyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$–$C_{18}$alkyl, $C_1$–$C_{18}$alkoxy, $C_1$–$C_{18}$alkylthio, di($C_1$–$C_4$alkyl)amino, phenyl, benzyl, benzoyl or by benzoyloxy or R₁ is a radical of formula II or III

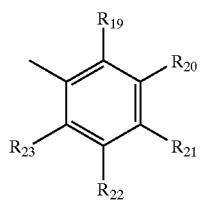
(II)

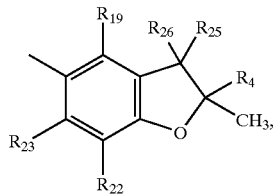
(III)

when n is 2,

R₁ is phenylene or naphthylene each unsubstituted or substituted by $C_1$–$C_4$alkyl or by fluorine; or is —R₆—X—R₇—, R₂, R₃, R'₄ and R₅ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals R₂ and R₃ or the radicals R₃ and R'₄ or the radicals R'₄ and R₅, together with the carbon atoms to which they are bonded, form a benzo ring, R'₄ is additionally —(CH₂)ₚ—COR₉ or —(CH₂)_q OH or, when R₃ and R₅ are hydrogen, R'₄ is additionally a radical of formula VI

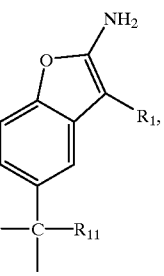
(VI)

wherein R₁ is as defined above for the case where n=1,

R₆ and R₇ are each independently of the other phenylene or naphthylene each unsubstituted or substituted by $C_1$–$C_4$alkyl, R₈ is $C_1$–$C_8$alkyl, R₉ is hydroxy,

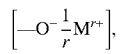

$C_1$–$C_{18}$alkoxy or

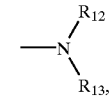

R₁₀ and R₁₁ are each independently of the other hydrogen, CF₃, $C_1$–$C_{12}$alkyl or phenyl, or R₁₀ and R₁₁, together with the carbon atom to which they are bonded, form a $C_5$–$C_8$cycloalkylidene ring unsubstituted or substituted by from 1 to 3 $C_1$–$C_4$alkyl groups;

R₁₂ and R₁₃ are each independently of the other hydrogen or $C_1$–$C_{18}$alkyl, R₁₄ is hydrogen or $C_1$–$C_{18}$alkyl, R₁₉, R₂₀, R₂₁, R₂₂ and R₂₃ are each independently of the others hydrogen, halogen, fluoro-substituted $C_1$–$C_{12}$alkyl; —CN,

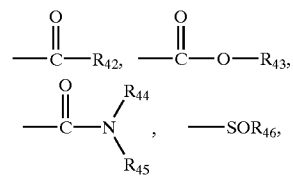

—SO₂R₄₆, SO₃R₄₆, hydroxy, $C_1$–$C_{25}$alkyl; $C_2$–$C_{25}$alkyl interrupted by oxygen, sulfur or by

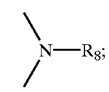

$C_1$–$C_{25}$alkoxy; $C_2$–$C_{25}$alkoxy interrupted by oxygen, sulfur or by

$C_1$–$C_{25}$alkylthio, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; di($C_1$–$C_4$alkyl)amino, $C_1$–$C_{25}$alkanoyl; $C_3$–$C_{25}$alkanoyl interrupted by oxygen, sulfur or by

$C_1$–$C_{25}$alkanoyloxy; $C_3$–$C_{25}$alkanoyloxy interrupted by oxygen, sulfur or by

$C_1$–$C_{25}$alkanoylamino, $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

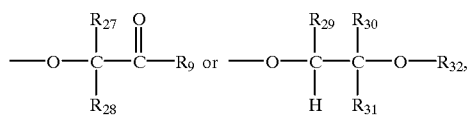

$R_{24}$ is hydrogen, $C_1$–$C_4$alkyl, or unsubstituted or $C_1$–$C_4$alkyl-substituted phenyl,
$R_{25}$ and $R_{26}$ are hydrogen, $C_1$–$C_4$alkyl or phenyl, with the proviso that at least one of the radicals $R_{25}$ and $R_{26}$ is hydrogen,
$R_{27}$ and $R_{28}$ are each independently of the other hydrogen, $C_1$–$C_4$alkyl or phenyl,
$R_{29}$ is hydrogen or $C_1$–$C_4$alkyl,
$R_{30}$ is hydrogen, unsubstituted or $C_1$–$C_4$alkyl-substituted phenyl; $C_1$–$C_{25}$alkyl; $C_2$–$C_{25}$alkyl interrupted by oxygen, sulfur or by

$C_7$–$C_9$phenylalkyl unsubstituted or substituted on the phenyl radical by from 1 to 3 $C_1$–$C_4$alkyl groups; or $C_7$–$C_{25}$phenylalkyl interrupted by oxygen, sulfur or by

and unsubstituted or substituted on the phenyl radical by from 1 to 3 $C_1$–$C_4$alkyl groups,
$R_{31}$ is hydrogen or $C_1$–$C_4$alkyl,
$R_{32}$ is hydrogen, $C_1$–$C_{25}$alkanoyl; $C_3$–$C_{25}$alkanoyl interrupted by oxygen, sulfur or by

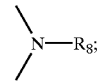

$C_2$–$C_{25}$alkanoyl substituted by a di($C_1$–$C_6$alkyl) phosphonate group; $C_6$–$C_9$cycloalkylcarbonyl, thenoyl, furoyl, benzoyl, or $C_1$–$C_{12}$alkyl-substituted benzoyl;

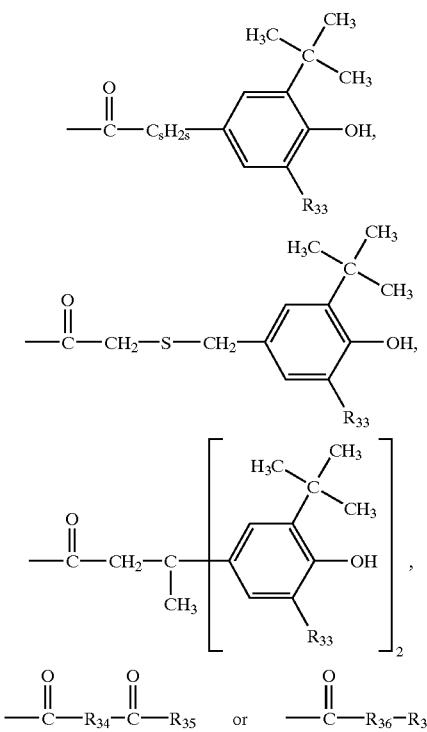

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

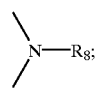

$C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

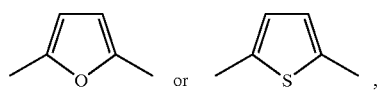

$R_{35}$ is hydroxy, $$\left[-O^-\frac{1}{r}M^{r+}\right],$$

$C_1$–$C_{18}$alkoxy or

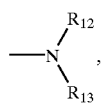

$R_{36}$ is oxygen, —NH— or

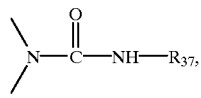

$R_{37}$ is $C_1$–$C_{18}$alkyl or phenyl,
$R_{42}$ is hydrogen, hydroxy,

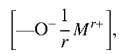

$C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

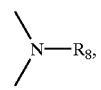

$R_{43}$ is $C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

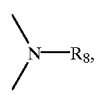

$R_{44}$ and $R_{45}$ are each independently of one another hydrogen, $C_1$–$C_{25}$alkyl, hydroxyl-substituted $C_2$–$C_{24}$alkyl; $C_3$–$C_{25}$alkyl which is interrupted by oxygen, sulfur or

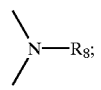

$C_7$–$C_9$phenylalkyl which is unsubstituted or is substituted on the phenyl ring by $C_1$–$C_4$alkyl; or $C_3$–$C_{24}$alkenyl; or $R_{44}$ and $R_{45}$, together with the nitrogen atom to which they are attached, form a 5-, 6- or 7-membered heterocyclic ring which is unsubstituted or is substituted by $C_1$–$C_4$alkyl or is interrupted by oxygen, sulfur or

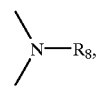

$R_{46}$ is hydrogen or $C_1$–$C_{25}$alkyl,
M is an r-valent metal cation,
X is a direct bond, oxygen, sulfur or —$NR_{14}$—,
n is 1 or 2,
p is 0, 1 or 2,
q is 1,2,3,4,5 or 6,
r is 1, 2 or 3, and
s is 0, 1 or 2; with the proviso that, when $R_2$, $R_3$, $R_5$, $R_{19}$, $R_{20}$, $R_{21}$, $R_{22}$ and $R_{23}$ are hydrogen,
$R'_4$ is not methylthio.

The preferred general symbols for the novel compounds of formula V correspond to those in the preferred general symbols set out hereinbefore for the process according to the invention for the preparation of compounds of formula I.

The compounds of the formula I are suitable for stabilizing organic materials against oxidative, thermal or light-induced degradation. Special attention is drawn to their excellent action as antioxidants in the stabilization of organic materials.

Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/ isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or o-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Further objects of the invention are therefore compositions comprising a) an organic material which is susceptible to oxidative, thermal or light-induced degradation, and b) at least one compound of the formula V.

Preferred organic materials are natural, semi-synthetic or, preferably, synthetic polymers.

Particularly referred organic materials are synthetic polymers, most preferably thermoplastic polymers. Especially preferred organic materials are polyacetals, polyolefins such as polypropylene or polyethylene, polyether/polyurethanes, polyesters such as polybutylene terephthalate, polycarbonates or vulcanisates.

To be singled out for special mention is the efficacy of the novel compounds of the formula I against oxidative or thermal degradation, especially under the action of heat which occurs during the processing of thermoplasts. The compounds of the formula I of this invention are therefore admirably suited for use as processing stabilizers.

The compounds of the formula I will preferably be added to the organic material to be stabilized in concentrations of 0.0005 to 10%, preferably 0.001 to 2%, typically 0.01 to 2%, based on the weight of said material.

In addition to comprising the compounds of the formula I, the inventive compositions may comprise further co-stabilizers, typically the following:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(a-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxy-benzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4- hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexal-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazine. N,N'-bis[2-(3-[3,5-di-tert-butyl-4-hydroxyphenyl]propionyloxy)ethyl]oxamide (Naugarde®XL-1, supplied by Uniroyal).

1.18. Ascorbic acid (vitamin C)

1.19. Aminic antioxidants, for example N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N, N-bis(2,2,6,6-tetra-methylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilizers 2.1. 2-(2'-Hydroxyphenyl)benzotriazoles, for example 2-(2'-hydroxy-5'-methylphenyl)benzo-triazole, 2-(3',5'-di-tert-butyl-2'-hydroxyphenyl)benzotriazole, 2-(5'-tert-butyl-2'-hydroxyphenyl)benzotriazole 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(as,-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyl-oxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'- tert-butyl-2'-hydroxy-5'-(2-isooctyloxycarbonylethyl) phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$]$_2$, where R=3'-tert-butyl-4'-hydroxy-5'-2H-benzotriazol-2-ylphenyl, 2-[2'-hydroxy-3'-(1,1,3,3-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxhenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,4-di-cumylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene) sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxylphenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The co-stabilizers are typically used in concentrations of 0.01 to 10%, based on the total weight of the material to be stabilized.

The novel compounds of the formula V can be used in particular together with phenolic antioxidants, light stabilizers and/or processing stabilizers.

Other preferred compositions comprise, in addition to compounds of the formula I, a compound of the organic phosphite or phosphonite type.

The fillers and reinforcing agents (point 12 of the list), such as, for example, talc, calcium carbonate, mica or kaolin, are added to the polyolefins, for example, in concentrations of from 0.01 to 40%, based on the total weight of the polyolefins to be stabilized.

The fillers and reinforcing agents (point 12 of the list), such as, for example, metal hydroxides, especially aluminium hydroxide or magnesium hydroxide, are added to the polyolefins, for example, in concentrations of from 0.01 to 60%, based on the total weight of the polyolefins to be stabilized.

Carbon black, as filler, is added to the polyolefins advantageously in concentrations of from 0.01 to 5%, based on the total weight of the polyolefins to be stabilized.

Glass fibres, as reinforcing agents, are added to the polyolefins advantageously in concentrations of from 0.01 to 20%, based on the total weight of the polyolefins to be stabilized.

Also of interest as yet further additives in the compositions according to the invention are alkaline earth metal salts of higher fatty acids, such as, for example, calcium stearate; calcium lactate and/or calcium stearoyl-2-lactylate.

As a conventional stabilizer combination for the processing of polymeric organic materials, such as, for example, polyolefins, into corresponding moulded articles, the combination of a phenolic antioxidant with a secondary antioxidant based on an organic phosphite or phosphonite is recommended. Depending on the substrate and process, however, many polyolefin processors are obliged to operate processes in the high-temperature range above approx. 280° C. The inclusion of a processing stabilizer of the formula V is particularly suitable for high-temperature applications, especially in the temperature range above 300° C. Technical materials and moulded articles for instance based on HD polyethylene, such as, for example, pipes and their technical variants (fittings), can be manufactured with a higher output and fewer rejects. A further advantage of the compounds of the formula V is also that they can be used in a very small amount, which results in a reduction in the overall antioxidant concentration compared with conventional stabilizer mixtures. For instance the use of a low concentration of a compound of the formula I allows the overall stabilizer concentration to be reduced by approximately a third in, for example, polyolefins, which at the same time represents an economic advantage.

The compounds of the formula V and other optional additives are incorporated into the organic polymeric material according to known methods, for example before or during shaping to moulded articles or alternatively by coating the organic polymeric material with a solution or dispersion of the compounds and subsequently evaporating the solvent. The compounds of the formual V can also be added to the materials to be stabilized in the form of a master batch which contains these compounds, typically in a concentration of, for example, from 2.5 to 25% by weight.

The compounds of the formula V may also be added before or during polymerization or before crosslinking.

In this connection, particular attention is drawn to the surprising feature that the novel compounds of the formula V inhibit discoloration, especially so-called pinking in the manufacture of e.g. polyurethane foams.

The compounds of the formula V, and where applicable further additives, may be incorporated into the material to be stabilized in pure form or encapsulated in waxes, oils or polymers.

The compounds of the formula V, and where applicable further additives, may also be sprayed onto the polymer to be stabilized. They are able to be used to dilute other additives (e.g. the above-mentioned conventional additives) or melts thereof, so that they can also be sprayed together with these additives onto the polymer to be stabilized. Application by spraying during the deactivation of the polymerization catalysts is especially advantageous, in which case spraying is conveniently effected with the vapour used for deactivation.

The materials stabilized in that manner may be used in an extremely wide variety of forms, e.g. in the form of films, fibres, tapes, moulding compounds or profiles, or as binders for surface-coatings, especially powder coatings, adhesives or cements.

The polyolefins stabilized in that manner may likewise be used in an extremely wide variety of forms, especially in the form of thick-layer polyolefin moulded articles that are in lasting contact with extracting media, such as, for example, pipes for liquids or gases, films, fibres, geomembranes, tapes, profiles or tanks.

The preferred thick-layer polyolefin moulded articles have a layer thickness of from 1 to 50 mm, especially from 1 to 30 mm, e.g. from 2 to 10 mm.

A preferred embodiment of this invention is therefore the use of compounds of the formula V as stabilizers for organic materials against oxidative, thermal or light-induced degradation.

The invention also relates to a process for stabilizing an organic material against oxidative, thermal or light-induced degradation, which comprises incorporating therein or applying thereto at least one compound of the formula V.

The invention relates also to compositions comprising a functional fluid, preferably from the series of lubricants, hydraulic fluids and metal-working fluids and also fuels for powering engines of the 4-stroke, Otto, 2-stroke, diesel, Wankel and orbital types, and at least one compound of the formula V.

The compounds of the formula V may preferably be used in lubricants and fuels as multifunctional stabilizers, that is to say they combine in themselves antioxidative, friction-reducing. extreme-pressure-protection and wear-protection action and also anti-corrosion properties.

Preferred lubricants and fuels and related products are engine oils, turbine oils, gear oils, hydraulic fluids, diesel or Otto fuels, metal-working fluids and lubricating greases.

Especially preferred lubricants are mineral oils, synthetic oils or mixtures thereof.

Products known per se are used as functional fluids from the series of lubricants, hydraulic fluids and metal-working fluids.

The lubricants and hydraulic fluids that come into consideration will be familiar to the person skilled in the art and are described in the relevant specialist literature, such as, for example, in Dieter Klamann, "Schmierstoffe und verwandte Produkte" [Lubricants and related products] (Verlag Chemie, Weinheim, 1982), in Schewe-Kobek, "Das Schmiermittel-Taschenbuch" [The lubricant handbook] (Dr. Alfred Hüthig-Verlag, Heidelberg, 1974) and in "Ullmanns Enzyklopädie der technischen Chemie" [Ullmann's Encyclopaedia of Industrial Chemistry], Vol. 13, pages 85–94 (Verlag Chemie, Weinheim, 1977).

The lubricants are especially oils and greases, for example based on a mineral oil. Oils are preferred.

A further group of lubricants that may be used are vegetable or animal oils, greases, tallows and waxes or mixtures thereof with one another or mixtures with the mentioned mineral or synthetic oils.

Vegetable and animal oils, greases, tallows and waxes are, for example, palm-kernel oil, palm oil, olive oil, rapeseed oil, rape oil, linseed oil, groundnut oil, soybean oil, cottonseed oil, sunflower oil, pumpkin seed oil, coconut oil, maize oil, castor oil, tree nut oil and mixtures thereof, fish oils, tallows obtained from slaughtered animals, such as beef tallow, neatsfoot oil and bone oil, and modified, epoxidised and sulfoxidised forms thereof, for example epoxidised soybean oil.

The mineral oils are based especially on hydrocarbon compounds.

Examples of synthetic lubricants include lubricants based on aliphatic or aromatic carboxy esters, polymeric esters, polyalkylene oxides, phosphoric acid esters, poly-alpha-olefins or silicones, a diester of a divalent acid with a monohydric alcohol, such as, for example, dioctyl sebacate or dinonyl adipate, a triester of trimethylolpropane with a monovalent acid or with a mixture of such acids, such as, for example, trimethylolpropane tripelargonate, trimethylolpropane tricaprylate or mixtures thereof, a tetraester of pentaerythritol with a monovalent acid or with a mixture of such acids, such as, for example, pentaerythritol tetracaprylate, or a complex ester of monovalent and divalent acids with polyhydric alcohols, for example a complex ester of trimethylolpropane with caprylic and sebacic acid, or a mixture thereof. Apart from mineral oils there are especially suitable, for example, poly-alpha-olefins, ester-based lubricants, phosphates, glycols, polyglycols and polyalkylene glycols, and also mixtures thereof with water.

Metal-working fluids and hydraulic fluids may be prepared on the basis of the same substances as those described above for the lubricants, such fluids frequently being emulsions of such substances in water or other liquids.

Lubricant and fuel compositions according to the invention are used, for example, in internal combustion engines, e.g. in motorised vehicles equipped with, for example, engines of the Otto, diesel, two-stroke, Wankel or orbital type.

The compounds of the formula V are readily soluble in lubricants and fuels, metal-working fluids and hydraulic fluids and are therefore especially suitable as additives for lubricants and fuels, metal-working fluids and hydraulic fluids.

As additives in lubricants, the compounds of the formula V are effective even in very small amounts. They are mixed in with the lubricants advantageously in an amount of from 0.01 to 5% by weight, preferably in an amount of from 0.05 to 3% by weight and very especially in an amount of from 0.1 to 2% by weight, in each case based on the lubricant.

The compounds of the formula V may be mixed in with the lubricants and fuels in a manner known per se. The compounds of the formula V are readily soluble, for example, in oils. It is also possible to prepare a so-called master batch, which may be diluted, as a function of use, with the appropriate lubricant or fuel to the concentrations suitable for use. In such cases concentrations above 1% by weight are possible.

The lubricants and fuels, metal-working fluids and hydraulic fluids may additionally comprise other additives that are added in order to improve their basic properties still further; such additives include: further antioxidants, metal passivators, rust inhibitors, viscosity index improvers, pour-point depressants, dispersants, detergents, coefficient of friction reducers, further extreme-pressure additives and anti-wear additives. Such further additives are added advantageously in an amount of from 0.01 to 5% by weight.

A number of such compounds can be found, for example, in the above list "1. Antioxidants", especially points 1.1 to 1.19. In addition, further additives may be mentioned by way of example:

Examples of further antioxidants:

Aliphatic or aromatic phosphites, esters of thiodipropionic acid or thiodiacetic acid or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators e.g. for copper, are:
a) Benzotriazoles and derivatives thereof, e.g. 2-mercaptobenzotriazole, 2,5-dimercaptobenzotriazole, 4- or 5-alkylbenzotriazoles (e.g. tolutriazole) and derivatives thereof, 4,5,6,7-tetrahydrobenzotriazole, 5,5'-methylenebis-benzotriazole; Mannich bases of benzotriazole or tolutriazole, such as 1-[di(2-ethylhexyl)aminomethyl] tolutriazole and 1-[di(2-ethylhexyl)aminomethyl] benzotriazole; alkoxyalkylbenzotriazoles, such as 1-(nonyloxymethyl)benzotriazole, 1-(1-butoxyethyl) benzotriazole and 1-(1-cyclohexyloxybutyl)-tolutriazole.
b) 1,2,4-Triazoles and derivatives thereof, e.g. 3-alkyl-(or-aryl-)1,2,4-triazoles, Mannich bases of 1,2,4-triazoles, such as 1-[di(2-ethylhexyl)aminomethyl]-1, 2,4-triazole; alkoxyalkyl-1,2,4-triazoles, such as 1-(1-butoxyethyl)-1,2,4-triazole; acylated 3-amino-1,2,4-triazoles.
c) Imidazole derivatives, e.g. 4,4'-methylenebis(2-undecyl-5-methyl)imidazole and bis[(N-methyl) imidazol-2-yl]carbinol-octyl ether.
d) Sulfur-containing heterocyclic compounds, e.g. 2-mercaptobenzothiazole, 2,5-dimercapto-1,3,4-thiadiazole, 2,5-dimercaptobenzothiadiazole and derivatives thereof; 3,5-bis[di(2-ethylhexyl) aminomethyl]-1,3,4-thiadiazolin-2-one.
e) Amino compounds, e.g. salicylidene-propylenediamine, salicylaminoguanidine and salts thereof.

Examples of rust inhibitors are:
a) Organic acids, their esters, metal salts, amine salts and anhydrides, e.g. alkyl- and alkenyl-succinic acids and their partial esters with alcohols, diols or hydroxycarboxylic acids, partial amides of alkyl- and alkenyl-succinic acids, 4-nonylphenoxyacetic acid, alkoxy- and alkoxyethoxy-carboxylic acids, such as dodecyloxy-acetic acid, dodecyloxy-(ethoxy)acetic acid and amine salts thereof, and also N-oleoyl-sarcosine, sorbitan monooleate, lead naphthenate, alkenylsuccinic acid anhydrides, e.g. dodecenylsuccinic acid anhydride, 2-(2-carboxyethyl)-1-dodecyl-3-methylglycerol and salts thereof, especially sodium and triethanolamine salts thereof.
b) Nitrogen-containing compounds, e.g.:
  i. Primary, secondary or tertiary, aliphatic or cycloaliphatic amines and amine salts of organic and inorganic acids, e.g. oil-soluble alkylammonium carboxylates, and 1-[N,N-bis(2-hydroxyethyl) amino]-3-(4-nonylphenoxy)propan-2-ol.
  ii. Heterocyclic compounds, e.g.: substituted imidazolines and oxazolines, e.g. 2-hepta-decenyl-1-(2-hydroxyethyl)-imidazoline.
c) Phosphorus-containing compounds, e.g.:
  Amine salts of phosphoric acid partial esters or phosphonic acid partial esters, zinc dialkyldithiophosphates.
d) Sulfur-containing compounds, e.g.:
  Barium dinonylnaphthalene sulfonates, calcium petroleum sulfonates, alkylthio-substituted aliphatic carboxylic acids, esters of aliphatic 2-sulfocarboxylic acids and salts thereof.
e) Glycerol derivatives, e.g.:
  Glycerol monooleate, 1-(alkylphenoxy)-3-(2-hydroxyethyl)glycerols, 1-(alkylphenoxy)-3-(2,3-dihydroxypropyl)glycerols, 2-carboxyalkyl-1,3-dialkylglycerols.

Examples of viscosity index improvers are:
Polyacrylates, polymethacrylates, vinylpyrrolidone/ methacrylate copolymers, polyvinylpyrrolidones, polybutenes, olefin copolymers, styrene/acrylate copolymers, polyethers.

Examples of pour-point depressants are:
Poly(meth)acrylates, ethylene/vinyl acetate copolymer, alkylpolystyrenes, fumarate copolymers, alkylated naphthalene derivatives.

Examples of dispersants/surfactants are:
Polybutenylsuccinic acid amides or imides, polybutenylphosphonic acid derivatives, basic magnesium, calcium and barium sulfonates and phenolates.

Examples of extreme-pressure and anti-wear additives are:

Sulfur- and/or phosphorus- and/or halogen-containing compounds, such as, for example, chlorinated paraffins, sulfurated olefins or vegetable oils (soybean/rape oil), alkyl- or aryl-di-or -tri-sulfides, zinc dialkyldithiophosphates, zinc dithiocarbamates such as zinc diamyldithiocarbamate, molybdenum dithioates such as molybdenum dithiocarbamates, triaryl phosphates such as tritolyl phosphate, tricresyl phosphate, phenyl phosphate isopropyl ester, amine salts of mono- or di-alkylphosphoric acids such as the amine salts of mono-/di-hexyl phosphate, amine salts of alkylphosphonic acids such as the amine salt of methylphosphonic acid, triaryl phosphites such as trisnonylphenyl] phosphite, dialkyl phosphites such as dioctyl phosphite, triaryl monothiophosphates such as triphenyl thionophosphate or tris[isononylphenyl] thionophosphate or tert-butylated triphenyl thionophosphate, substituted trialkyl mono- or di-thiophosphates such as diisopropoxyphosphinothioyl)thio]propionate or butylene-1,3-bis[(diisobutoxyphosphinothioyl)propionate, trithiophosphates such as trithiophosphoric acid S,S,S-tris (isooctyl-2-acetates), amine salts of 3-hydroxy-1,3-thiaphosphetane-3-oxide, benzotriazoles or derivatives thereof such as bis(2-ethylhexyl)aminomethyl-tolutriazole, dithiocarbamates such as methylene-bis-dibutyldithiocarbamate, derivatives of 2-mercaptobenzothiazole such as 1-[N,N-bis(2-ethylhexyl) aminomethyl]-2-mercapto-1H-1,3-benzothiazole, derivatives of 2,5-dimercapto-1,3,4-thiadiazole such as 2,5-bis (tert-nonyldithio)-1,3,4-thiadiazole.

Examples of coefficient of friction reducers are:

Lard oil, oleic acid, tallow, rape oil, sulfurated fats, amines. Further examples are given in EP-A-0 565 487.

Examples of special additives for use in water/oil metal-working fluids and hydraulic fluids are:

Emulsifiers: petroleum sulfonates, amines, such as polyoxyethylated fatty amines, non-ionic surface-active substances;

buffers: alkanolamines;

biocides: triazines, thiazolinones, tris-nitromethane, morpholine, sodium pyridenethol;

speed improvers: calcium and barium sulfonates;

Examples of fuel additives:

Fuel additives are described in Kirk-Othmer, Encyclopedia of Chemical Technology, Vol 12, 1994 and in this instance are essentially petrol and diesel additives:

Petrol: dyes, especially azo dyes;

Antioxidants: aminic, especially para-phenylenediamines, or phenolic, e.g. 2,6-di-tert-butyl-phenol, as described above;

Metal deactivators: especially N,N'-disalicylidene-1,2-propane, benzotriazole, EDTA;

Rust inhibitors: for example carboxylic acids, sulfonates, amines or amine salts;

Dispersants: e.g. esters, high-molecular-weight amines, Mannich bases, succinimides, borated succinimides;

Detergents: for example fatty acid amides, nonpolymeric amines, polybutene succinimides, polyether amines, low-molecular-weight amines, sulfonates, salicylic acid derivatives;

Demulsifiers: for example long-chain alcohols or phenols containing poly-ethylene or-butylene groups;

Antiknock agents: tetralkyl lead, manganese methylcyclopentadienyltricarbonyl;

Oxygen compounds: esters of vegetable oils, ethers, alcohols for improving burn behaviour;

Diesel: ignition improvers (cetane improvers), e.g. alkyl nitrates, ether nitrates, alkyl diglycol nitrates, organic peroxides;

Stabilizers for, especially, cracked diesel: amines and other N-containing compounds that act as radical traps.

Especially preferred further additives in lubricants are aminic antioxidants, especially mixtures of mono- and di-alkylated tert-butyl-/tert-octyl-diphenylamines.

The present invention relates also to the use of the compounds of the formula V for stabilizing organic materials, especially as additives in lubricants and fuels, hydraulic fluids or metal-working fluids, preferably in hydraulic oils and gear oils. The use according to the invention includes protection of the metal components to be lubricated against mechanical attrition (wear protection) and corrosion protection activity and also antioxidation activity—with respect both to the lubricant and to the metal components.

The present invention accordingly relates also to a method for improving the properties, during use, of organic materials, especially lubricants and fuels, metal-working fluids and hydraulic fluids, wherein a compound of the formula V is added to those materials.

The compounds of formula V are also suitable as scavengers for the oxidized developer (Dox scavengers) in color photographic material.

The photographic materials according to this invention comprise a support bearing at least one layer of a light-sensitive silver halide emulsion.

Examples of color photographic materials according to this invention are color negative films, color reversal films, color positive films, color photographic paper, color reversal photographic paper, color-sensitive materials for the dye diffusion transfer process or the silver dye bleach process.

Of especial interest is a color photographic recording material comprising, on a base, at least one blue-sensitive silver halide emulsion layer containing at least one yellow dye providing compound, at least one green-sensitive silver halide emulsion layer containing at least one magenta dye providing compound, at least one red-sensitive silver halide emulsion layer containing at least one cyan dye providing compound, and customary (non light sensitive) top layer(s) and interlayers separating the light-sensitive layers.

The layers of the color photographic material can be arranged in various orders as is well known in the art.

The compounds of the formula V can be contained in any of the layers of the photographic material, i.e. in any of the light sensitive silver halide emulsion layers or in a non light sensitive layer. For use as a Dox scavenger, the compound of the formula V is preferably contained in one or more non light sensitive layers. In this case, the light sensitive layers may contain a lower concentration of a compound of the formula I or none.

The compounds of the formula V are preferably incorporated in an interlayer, especially a non-photosensitive interlayer, adjacent to the green-sensitive layer containing a magenta coupler. Preferred color photographic materials within this invention are those wherein the magenta coupler is of the pyrazolo-azole type, e.g. as disclosed in U.S. Pat. No. 5,538,840, column 49, line 51, until column 69, line 27, and publications cited therein; this section of U.S. Pat. No. 5,538,840 is hereby incorporated by reference.

Also preferred is a color photographic material, wherein the silver halide emulsion contains at least 95 mol-% AgCl.

In general, the compounds of the formula V are contained in the photographic material in an amount from 10 to 1000 mg/m$^2$, especially from 30 to 500 mg/m$^2$.

The compounds of formula V can be milled with polymers (e.g. PVS, polyester, polyvinyl alcohol etc.) and placed in a layer thus preventing their migration to adjacent layers. Also, compounds of formula V containing a suitable functional group (e.g. ester, hydroxy) can be reacted with a polymer, e.g. a polyvinyl alcohol or polyester, in order to attach them chemically. This form will reduce their migrating tendency.

Typical bases for the photographic material include polymeric films and paper (including polymer-coated paper). Details regarding supports and other layers of color photographic recording materials can be found in Research Disclosure, Item 36544, September 1994.

Essential constituents of the photographic emulsion layers are binders, silver halide particles and color couplers. Details regarding the constituents of the light sensitive layers and other (non light sensitive) layers such as top layers and interlayers separating the silver halide emulsion layers can be found in Research Disclosure, Item 38957, September 1996.

The invention therefore also pertains to a color photographic material comprising a compound of the formula V, and to the use of a compound of the formula V as an additive in a color photographic material.

The invention also partains to a process for preventing migration of the oxidized developer in a color photographic material from one color sensitive layer to another by incorporating a compound of the formula V into said material.

The compounds of the formula V of the present invention are of special advantage when incorporated into photographic materials containing magenta couplers of the pyrazolotriazole class.

Examples for especially suitable yellow, magenta and cyan couplers to be used in combination with compounds of the present invention are as given in U.S. Pat. No. 5,538,840, column 33, line 3, until column 73, line 34, and publications cited therein. These passages are hereby incorporated by reference.

The compounds of the formula V which can be used in the context of this invention can be incorporated into the color photographic recording material, on their own or together with the color coupler and with or without further additives, by pre-dissolving them in high-boiling organic solvents. Preference is given to the use of solvents which boil at higher than 160° C. Typical examples of these solvents are the esters of phthalic acid, phosphoric acid, citric acid, benzoic acid or of fatty acids, and also alkylamides and phenols.

Further details on the structure of the color photographic material of the invention, and the components or further additives which can be employed in the novel material, can be found, inter alia, in U.S. Pat. No. 5,538,840, column 27, line 25, to column 33, line 2; and further in U.S. Pat. No. 5,538,840 from column 74, line 18, to column 106, line 16; and in U.S. Pat. No. 5,780,625, column 12, line 6, until column 57, line 6, and the publications cited in these 2 references; these passages of U.S. Pat. No. 5,538,840 and U.S. Pat. No. 5,780,625 are hereby incorporated by reference. Other useful information, how compounds of the formula I can be used in photographic material, can be taken from EP-A-0 871 066, page 10, line 10, until page 11, line 32, especially the references cited therein.

The photographic layers in the material of this invention may also include UV absorbers, which screen out the UV light and therefore protect the dyes, the couplers or other components against photodegradation. Hydroquinone compounds according to this invention may be contained in those layers where UV absorbers are present.

UV absorbers preferably to be used in the novel material or within the process of present invention include benzotriazoles, 2-hydroxybenzophenones, oxanilides, cyanoacrylates, salicylic esters, acrylonitrile derivatives, thiazolines and 2-hydroxyphenyltriazines.

GB-A-2,319,523 describes from page 49, line 21, until page 73, line 2, further details of the color photographic material, especially couplers (page 52, line 1, until page 56, line 22), UV absorbers (page 56, line 25, until page 68, line 1) and dark stabilizers (page 68, line 2, until page 73, line 2). Preferred UV absorbers of the 2-hydroxyphenyltriazine class are also described in detail, for example, in U.S. Pat. No. 5,668,200, column 1, line 30, until column 7, line 55, and as specific examples from column 26, line 31, until column 32, last line, and, together with some advantageous UV absorbers of the benzotriazole class, in U.S. Pat. No. 5,300,414, column 2 to column 10, line 54. These sections of U.S. Pat. No. 5,668,200 and U.S. Pat. No. 5,300,414 are hereby incorporated by reference.

The compounds of formula V may be used in combination with any known Dox scavengers such as hydrazines, hydrazides, hydroquinones of e.g. formula HQ-1 or HQ-2; 6-hydroxy-chromanes of e.g. formula A-3, or hydroxylamines of e.g. formula A-4

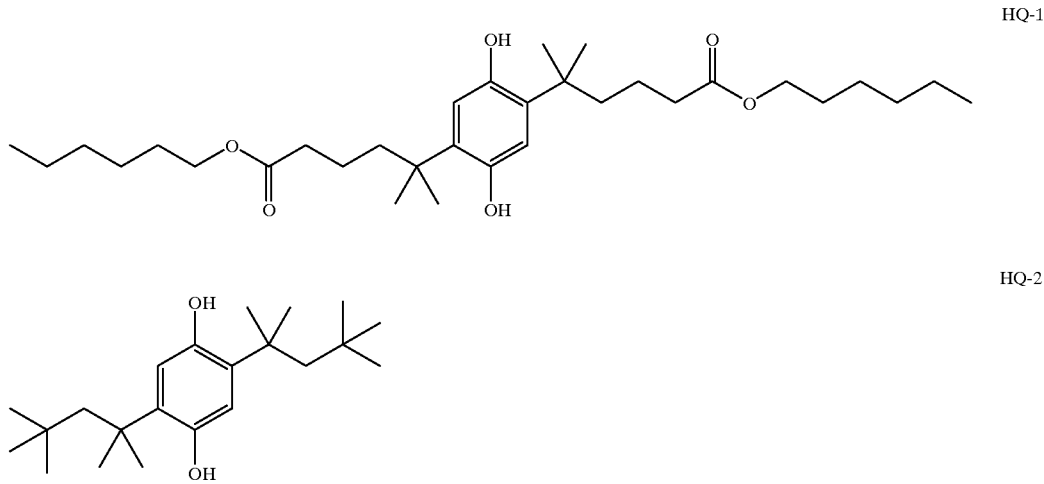

HQ-1

HQ-2

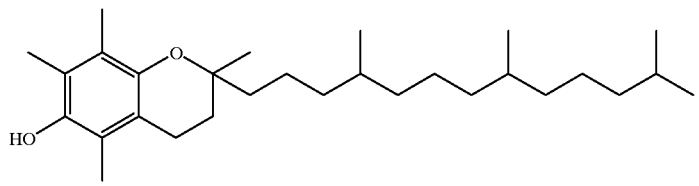

A-3

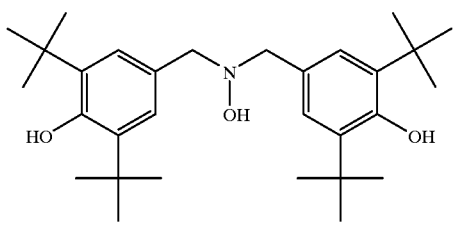

A-4

As silver halide emulsions it is possible to use customary silver chloride, silver bromide or silver iodide emulsions or mixtures thereof, such as silver chlorobromide and silver chloroiodide emulsions, in which the silver halides may have all known crystal forms. The use of silver chloride emulsions is accorded particular importance in the material of this novel process. The preparation of such emulsions and their sensitization are described in Research Disclosure, Item 307105, November 1989.

The compounds of the formula V may preferably also be used as stabilizers for ethylenically unsaturated resins against premature polymerization or crosslinking of the resins during transport or storage.

Preferred ethylenically unsaturated resins are for example liquid or resin-like monomers, oligomers, co-oligomers, polymers of co-polymers or mixtures thereof, which possess at least one ethylenically unsaturated bond and which are photo-polymerisable or curable with UV light.

The following Examples illustrate the invention further. Parts or percentages relate to weight.

EXAMPLE 1

Process for the preparation of 5,7-di-tert-butyl-3-phenyl-3H-benzofuran-2-one (compound (101), Table 1).

a) Preparation of 2-amino-3-phenyl-5,7-di-tert-butyl-benzofurane (compound (301), Table 3).

A solution of 0.98 g (20,0 mmol) of sodium cyanide in 2.0 ml of water is added to a solution of 3.39 g (10,0 mmol) of 2,4-di-tert-butyl-6-(dimethylaminophenyl-methyl)-phenol [compound (201), Table 2, prepared according to Example 2a in WO-A-99/67232] in 10 ml of sulfolane. The reaction mixture is then maintained at 120° C. for one hour. After cooling to room temperature, the reaction mixture is poured into 80 ml tert-butyl-methylether and washed three times with water. The organic phases are combined, dried over sodium sulfate and concentrated using a vacuum rotary evaporator. The residue yields 3.20 g (99%) of 2-amino-3-phenyl-5,7-di-tert-butyl-benzofurane (compound (301), Table 3), m.p. 174–178° C.

Compounds (304) to (323) [Table 3] are obtained in analogy to Example 1a using compounds (204) to (223) [Table 2] instead of compound (201).

b) Preparation of 5,7-di-tert-butyl-3-phenyl-3H-benzofuran-2-one (compound (101), Table 1).

4.8 ml (9.58 mmol) of 2N HCl is added at room temperature to a solution of 3.08 g (9.58 mmol) of 2-amino-3-phenyl-5,7-di-tert-butyl-benzofurane [compound (301), Table 3, prepared according to Example 1a] in 10 ml iso-propanol and stirred at room temperature for 90 minutes. The precipitate is filtered and washed with isopropanol. Crystallization of the residue from isopropanol yields 2.62 g (85%) of 5,7-di-tert-butyl-3-phenyl-3H-benzofuran-2-one (compound (101), Table 1), m.p. 116–119° C.

Compounds (104) to (123) [Table 1] are obtained in analogy to Example 1b using compounds (304) to (323) [Table 3] instead of compound (301).

EXAMPLE 2

Process for the preparation of 5,7-di-tert-butyl-3-(3,4-dimethylphenyl)-3H-benzofuran-2-one (compound (102), Table 1).

a) Preparation of 2-amino-5,7-di-tert-butyl-3-(3,4-dimethylphenyl)-benzofurane (compound (302), Table 3).

A solution of 0.25 g (5,00 mmol) of sodium cyanide in 0.5 ml of water is added to a solution of 0.37 g (1,00 mmol) of 2,4-di-tert-butyl-6-[dimethylamino-(3,4-dimethylphenyl-methyl)-phenol [compound (202), Table 2, prepared according to Example 1a in WO-A-99/67232] in 5 ml of sulfolane. The reaction mixture is then maintained at 120° C. for one hour. After cooling to room temperature, the reaction mixture is diluted with diethyl ether and washed three times with water. The organic phases are combined, dried over sodium sulfate and concentrated using a vacuum rotary evaporator. Crystallisation of the residue from hexane yields 0.28 g (86%) of 2-amino-5,7-di-tert-butyl-3-(3,4-dimethylphenyl)-benzofurane (compound (302), Table 3), m.p. 128–130° C.

b) Preparation of 5,7-di-tert-butyl-3-(3,4-dimethylphenyl)-3H-benzofuran-2-one (compound (102), Table 1).

0.35 ml (0.70 mmol) of 2N HCl is added at room temperature to a solution of 0.22 g (0.63 mmol) of 2-amino-5,7-di-tert-butyl-3-(3,4-dimethylphenyl)-benzofurane [compound (302), Table 3, prepared according to Example 2a] in 5 ml methanol and stirred at room temperature for 2 hours. The reaction mixture is diluted with water and extracted three times with ethyl acetate. The organic phases are combined, dried over sodium sulfate and concentrated using a vacuum rotary evaporator. Crystallisation of the residue from ethanol yields 200 mg (96%) of 5,7-di-tert-butyl-3-(3,4-dimethylphenyl-3H-benzofuran-2-one (compound (102), Table 1), m.p. 130–132° C.

EXAMPLE 3

Process for the preparation of 5,7-di-tert-butyl-3-(3,4-dimethoxyphenyl)-3H-benzofuran-2-one (compound (103), Table 1).

a) Preparation of 2-amino-5,7-di-tert-butyl-3-(3,4-dimethoxyphenyl)-benzofurane (compound (303), Table 3).

A solution of 0.33 g (6,80 mmol) of sodium cyanide in 0.5 ml of water is added to a solution of 0.50 g (1,36 mmol) of 2,4-di-tert-butyl-6-[dimethylamino-(3,4-dimethoxyphenyl-methyl)-phenol [compound (203), Table 2, prepared in analogy to Example 1a in WO-A-99/67232] in 5 ml of sulfolane. The reaction mixutre is then maintained at 105° C. for one hour. After cooling to room temperature, the reaction mixture is diluted with ethyl acetate and washed three times with water. The organic phases are combined, dried over sodium sulfate and concentrated using a vacuum rotary evaporator. Crystallisation of the residue from hexane yields 0.47 g (95%) of 2-amino-5,7-di-tert-butyl-3-(3,4-dimethoxyphenyl)-benzofurane (compound (303), Table 3), m.p. 172–174° C.

b) Preparation of 5,7-di-tert-butyl-3-(3,4-dimethoxyphenyl)-3H-benzofuran-2-one (compound (103), Table 1).

0.20 ml (0.40 mmol) of 2N HCl is added at room temperature to a solution of 50 mg (0.13 mmol) of 2-amino-5,7-di-tert-butyl-3-(3,4-dimethoxyphenyl)-benzofurane [compound (303), Table 3, prepared according to Example 3a] in 2 ml methanol and stirred at room temperature for one hour. The reaction mixture is diluted with water and extracted three times with ethyl acetate. The organic phases are combined, dried over sodium sulfate and concentrated using a vacuum rotary evaporator. The residue yields 41 mg (82%) of 5,7-di-tert-butyl-3-(3,4-dimethoxyphenyl-3H-benzofuran-2-one (compound (103), Table 1), viscous oil.

TABLE 1

| No. | Compound |
|---|---|
| 101 | |
| 102 | |
| 103 | |

TABLE 1-continued
| No. | Compound |
|-----|----------|
| 104 | 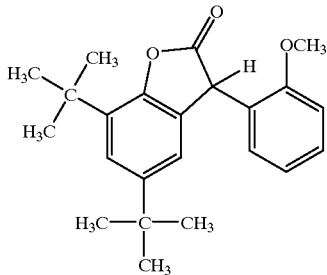 |
| 105 | 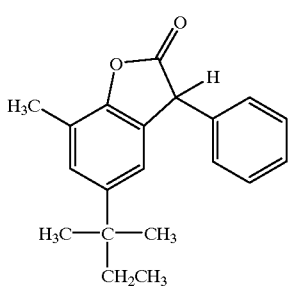 |
| 106 | 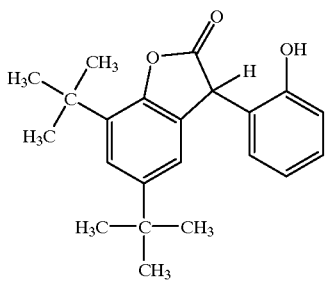 |
| 107 | 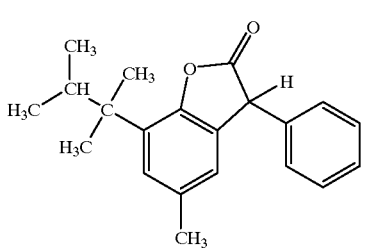 |
| 108 | 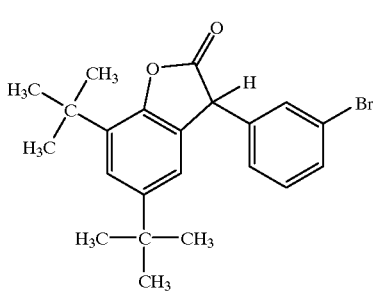 |

TABLE 1-continued
| No. | Compound |
|---|---|
| 109 | 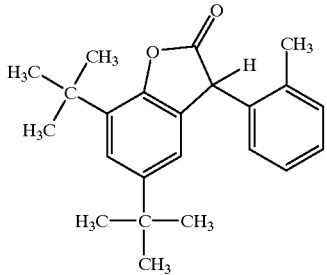 |
| 110 | 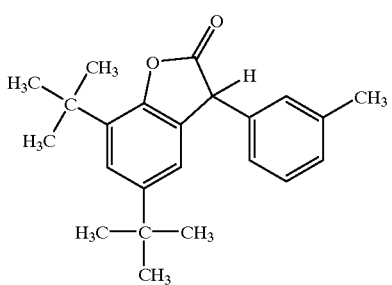 |
| 111 | 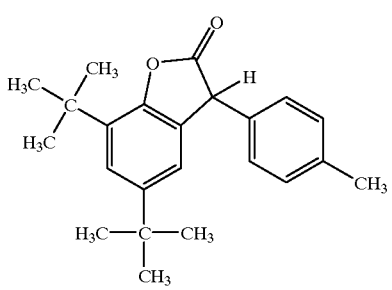 |
| 112 | 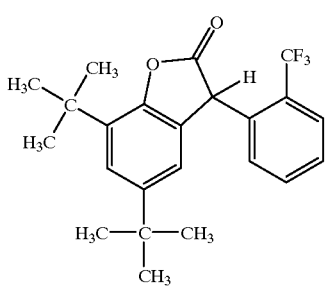 |
| 113 | 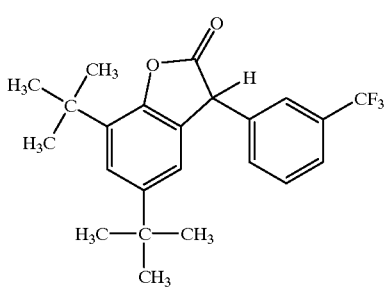 |

TABLE 1-continued
| No. | Compound |
|---|---|
| 114 | 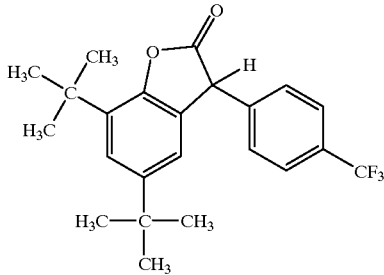 |
| 115 | 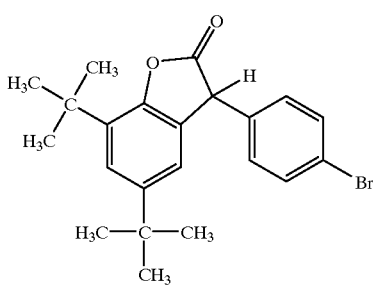 |
| 116 | 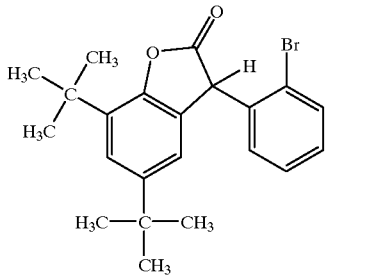 |
| 117 | 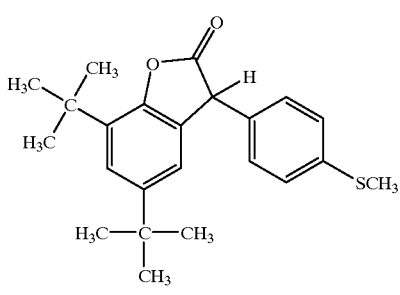 |
| 118 | 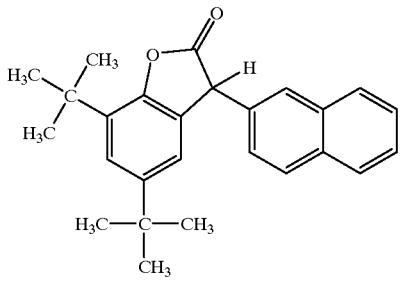 |

TABLE 1-continued

| No. | Compound |
|---|---|
| 119 | |
| 120 | |
| 121 | |
| 122 | |
| 123 | |

TABLE 2
| No. | Compound |
|---|---|
| 201 | 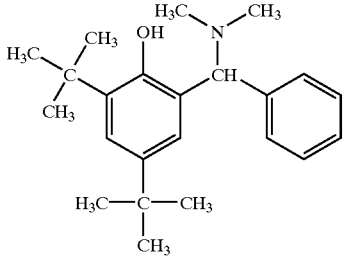 |
| 202 | 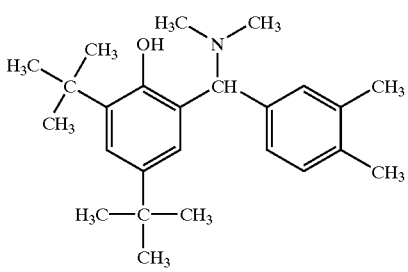 |
| 203 | 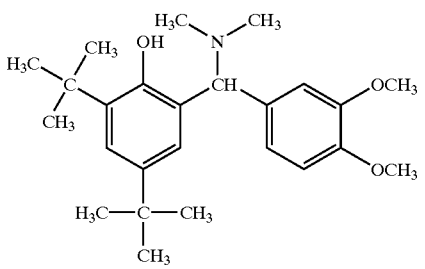 |
| 204 | 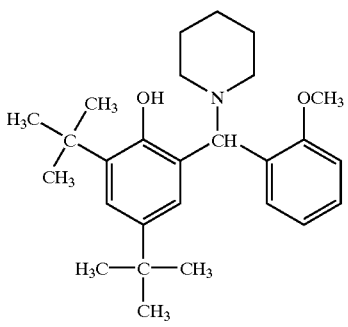 |
| 205 | 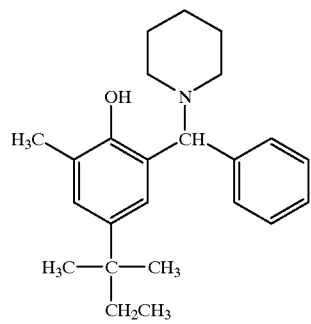 |

TABLE 2-continued
| No. | Compound |
|---|---|
| 206 | 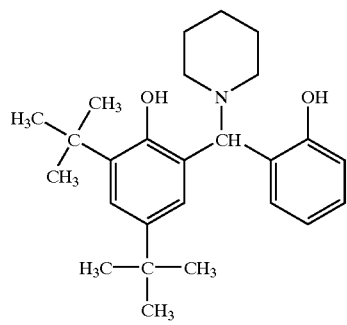 |
| 207 | 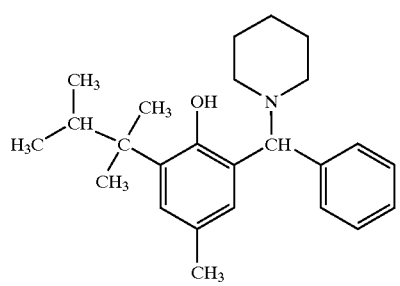 |
| 208 | 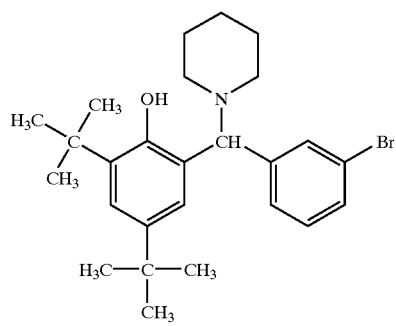 |
| 209 | 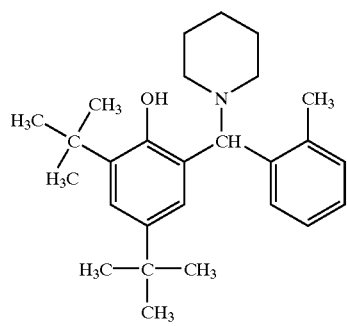 |

TABLE 2-continued
| No. | Compound |
|---|---|
| 210 | 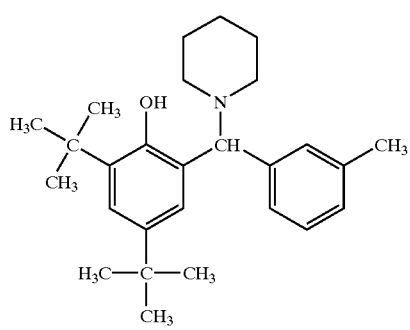 |
| 211 | 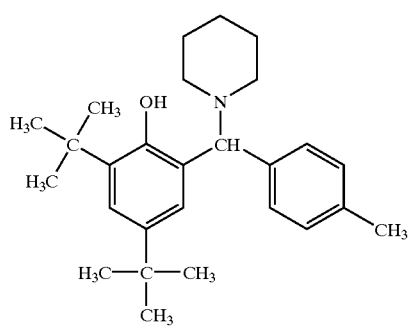 |
| 212 | 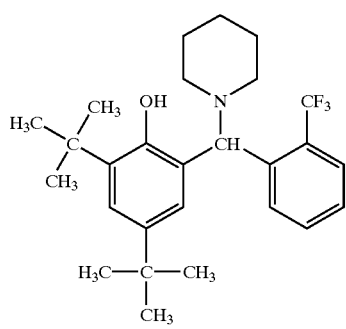 |
| 213 | 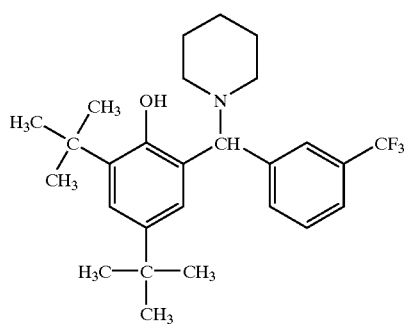 |

TABLE 2-continued
| No. | Compound |
|---|---|
| 214 | 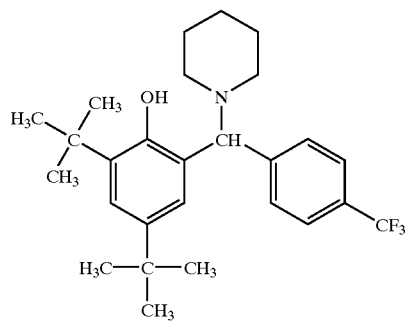 |
| 215 | 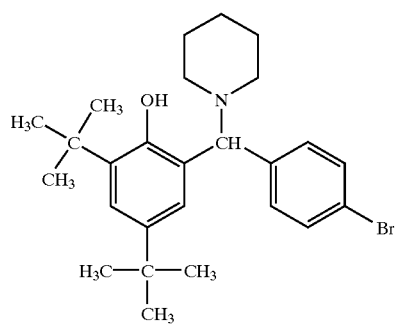 |
| 216 | 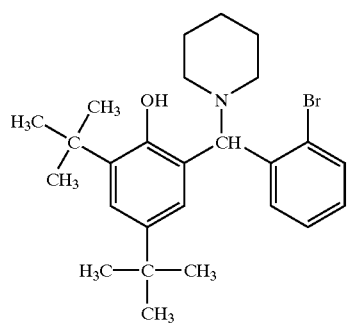 |
| 217 | 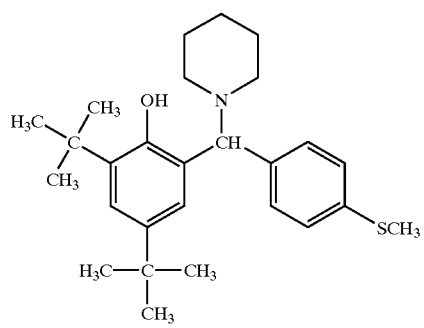 |

TABLE 2-continued
| No. | Compound |
|---|---|
| 218 | 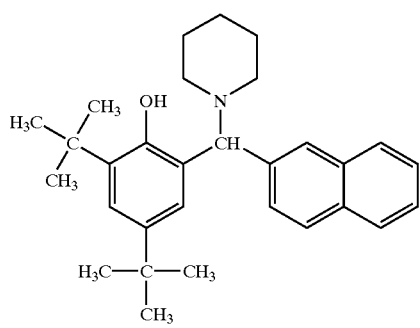 |
| 219 | 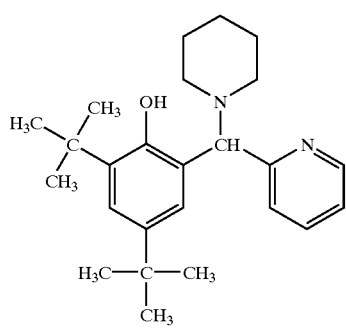 |
| 220 | 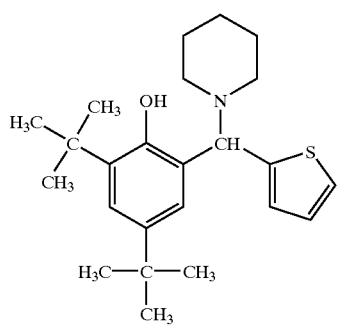 |
| 221 | 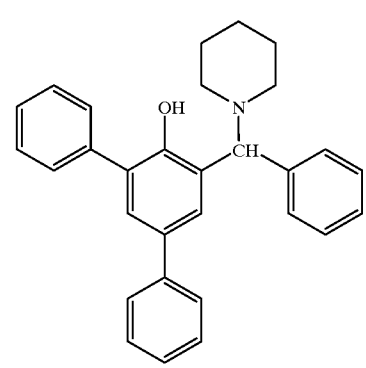 |

TABLE 2-continued
| No. | Compound |
|---|---|
| 222 | 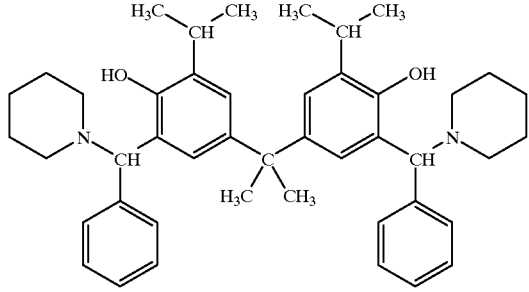 |
| 223 | 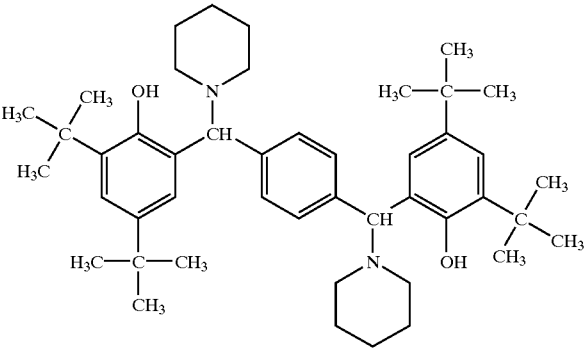 |
TABLE 3
| No. | Compound | m.p. (° C.) |
|---|---|---|
| 301 | 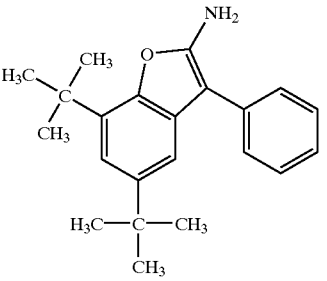 | 176—178 |
| 302 | 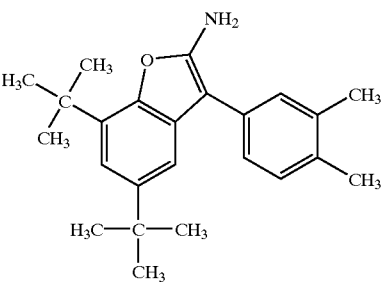 | 128—130 |

TABLE 3-continued
| No. | Compound | m.p. (° C.) |
|---|---|---|
| 303 | 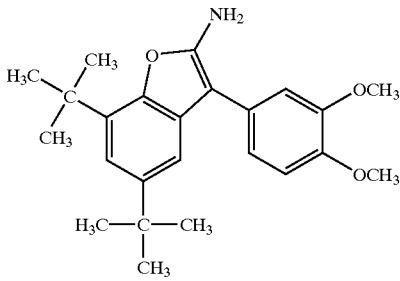 | 172—174 |
| 304 | 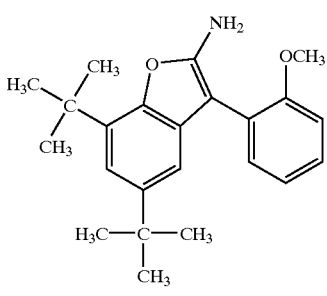 | resin |
| 305 | 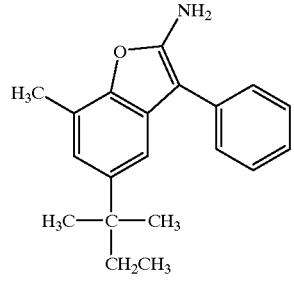 | resin |
| 306 | 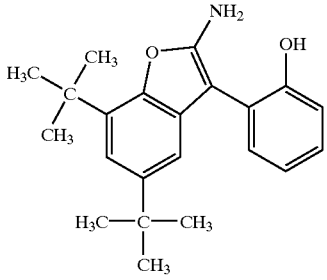 | 128—130 |
| 307 | 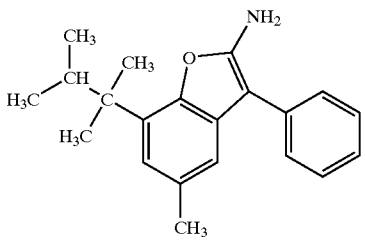 | 99—100 |

TABLE 3-continued

| No. | Compound | m.p. (° C.) |
|---|---|---|
| 308 | 7-tert-butyl-5-tert-butyl-3-(3-bromophenyl)-2-aminobenzofuran | 109—111 |
| 309 | 7-tert-butyl-5-tert-butyl-3-(2-methylphenyl)-2-aminobenzofuran | 132—134 |
| 310 | 7-tert-butyl-5-tert-butyl-3-(3-methylphenyl)-2-aminobenzofuran | 123—125 |
| 311 | 7-tert-butyl-5-tert-butyl-3-(4-methylphenyl)-2-aminobenzofuran | 172—173 |
| 312 | 7-tert-butyl-5-tert-butyl-3-(2-trifluoromethylphenyl)-2-aminobenzofuran | resin |

TABLE 3-continued

| No. | Compound | m.p. (° C.) |
|---|---|---|
| 313 | 7-tert-butyl-5-tert-butyl-3-(3-trifluoromethylphenyl)-2-aminobenzofuran | 101—103 |
| 314 | 7-tert-butyl-5-tert-butyl-3-(4-trifluoromethylphenyl)-2-aminobenzofuran | 127—132 |
| 315 | 7-tert-butyl-5-tert-butyl-3-(4-bromophenyl)-2-aminobenzofuran | 156—158 |
| 316 | 7-tert-butyl-5-tert-butyl-3-(2-bromophenyl)-2-aminobenzofuran | resin |
| 317 | 7-tert-butyl-5-tert-butyl-3-(4-methylthiophenyl)-2-aminobenzofuran | 140—141 |

TABLE 3-continued
| No. | Compound | m.p. (° C.) |
|---|---|---|
| 318 | 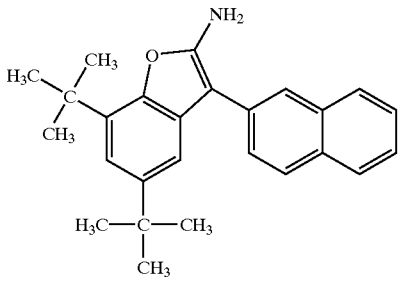 | 168—171 |
| 319 | 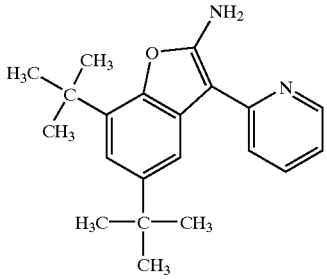 | 121—123 |
| 320 | 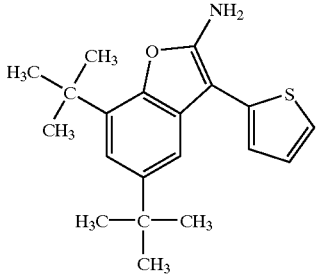 | 124—125 |
| 321 | 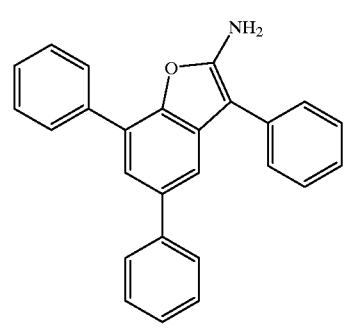 | |
| 322 | 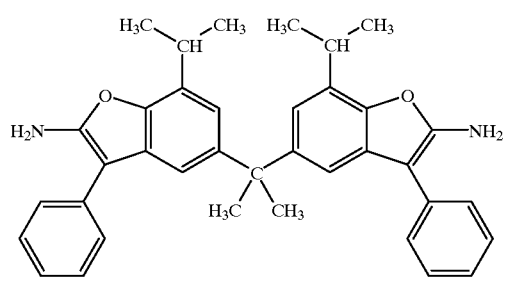 | |

TABLE 3-continued

| No. | Compound | m.p. (° C.) |
|---|---|---|
| 323 | (structure) | |

EXAMPLE 4

Stabilization of multiple-extruded polypropylene.

1.3 kg of polypropylene powder (Profax 6501), which has been prestabilized with 0.025% of Irganox®1076 (n-octadecyl 3-[3,5-di-tert-butyl-4-hydroxyphenyl] propionate) (melt index 3.2 g/10 min, measured at 230° C./2.16 kg) are blended with 0.05% of Irganox®1010 (pentaerythritol tetrakis[3-(3,5-di-tert-butyl-4-hydroxyphenyl)propionate]), 0.05% of calcium stearate, 0.03% of DHT 4A® (Kyowa Chemical Industry Co., Ltd., [Mg$_{4.5}$Al$_2$(OH)$_{13}$CO$_3$·3.5 H$_2$O]) and 0.05% of compound of Table 3. This blend is then extruded in an extruder having a cylinder diameter of 20 mm and a length of 400 mm at 100 rpm, the 3 heating zones being adjusted to the following temperatures: 260, 270, 280° C. The extrudate is cooled by drawing it through a water bath and is then granulated. This granulate is repeatedly extruded. After 3 extrusions, the melt index is measured (at 230° C./2.16 kg). A substantial increase in the melt index denotes pronounced chain degradation, i.e. poor stabilization. The results are summarized in Table 4.

TABLE 4

| Compound of Table 1 | Melt index after 3 extrusions |
|---|---|
| — | 17.8 |
| 301 | 4.9 |
| 302 | 4.9 |
| 311 | 4.9 |
| 313 | 4.9 |
| 319 | 4.9 |

EXAMPLE 5

Stabilization of polyethylene during processing.

100 parts of polyethylene powder (Lupolen® 5260 Z) are blended with 0.05 part of Irganox® 1010 (pantaerythritol tetrakis[3-(3,5-di-tert-butyl-4-hydroxyphenyl)propionate]) and 0.05 part of a compound of Table 3 and the blend is kneaded in a Brabender plastograph at 220° C. and 50 rpm. During this time the kneading resistance is recorded continuously as torque. In the course of the kneading time the polymer begins to crosslink after prolonged constancy, as can be determined by the rapid increase in torque. The time taken until a marked increase in torque is shown in Table 5 as a measure of the stabilizing action. The longer this time is the better the stabilizing action.

TABLE 5

| Compound of Table 1 | Time until increase in torque (min) |
|---|---|
| — | 9.7 |
| 301 | 27.4 |
| 302 | 27.4 |
| 307 | 27.3 |
| 310 | 27.4 |
| 320 | 27.3 |

EXAMPLE 6

Stabilization of multiple-extruded polypropylene at high temperature.

1.5 kg of polypropylene powder (Profax 6501), which has been prestabilized with 0.008% of Irganox®1076 (n-octadecyl 3-[3,5-di-tert-butyl-4-hydroxyphenyl] propionate) (melt index 3.2 g/10 min, measured at 230° C./2.16 kg) are blended with 0.05% of Irganox®1010 (pentaerythritol tetrakis[3-(3,5-di-tert-butyl-4-hydroxyphenyl)propionate]), 0.10% of calcium stearate and 0.015 to 0.100% of stabilizer or stabilizer mixture according to Table 6. This blend is then extruded in an extruder having a cylinder diameter of 20 mm and a length of 400 mm at 100 rpm, the 3 heating zones being adjusted to the following temperatures: 280, 320, 340° C. The extrudate is cooled by drawing it through a water bath and is then granulated. This granulate is repeatedly extruder. After 5 extrusions, the melt index is measured (at 230° C./2.16 kg). A substantial increase in the melt index denotes pronounced chain degradation, i.e. poor stabilization. The results are summarized in Table 6.

TABLE 6

| Stabilizers | Concentration in % (by weight) | Melt index after 5 extrusions 280° C. | 320° C. | 340° C. |
|---|---|---|---|---|
| Irgafos ® 168[a] | 0.100 | 9.8 | 44.0 | 80.4 |
| Sandostab ® P-EPQ[b] | 0.050 | 6.4 | 24.1 | 61.9 |
| Compound (301) | 0.015 | 8.1 | 19.8 | 22.7 |
| Irgafos ® 168[a] | 0.045 | 7.3 | 23.1 | 26.1 |
| Compound (301) | 0.005 | | | |
| Sandostab ® P-EPQ[b] | 0.045 | 5.7 | 16.0 | 24.9 |
| Compound (301) | 0.005 | | | |

For footnotes [a] and [b] see the end of Table 21.

EXAMPLE 7

Preparation of polyether/polyurethane soft foams as well as the stabilization thereof.

Exactly 470 mg (0.3%, based on the polyol) of a stabilizer mixture of this invention is dissolved in 157 g of an antioxidant-free polyether/polyol, Lupranol®2045 (trifunctional poly-ether/polyol having primary hydroxyl groups; hydroxyl number 35 mg KOH/g, water content less than 0.1%, acid number less than 0.1 mg KOH/g). 10.24 g of a solution consisting of 1.74 g Tecostab® (polysilicone supplied by Goldschmidt, Germany], 0.48 g diazabicyclooctane (amine catalyst) and 0.8 g of water are added and the reaction mixture is stirred vigorously for 60 seconds at 100 rpm. 3.2 g of a solution of 0.32 g of tin octoate (catalyst) in 2.9 g of the above polyol is added and the reaction mixture is again stirred vigorously for 60 seconds at 100 rpm. With vigorous stirring, 98 g of an isocyanate (Lupranat®80, supplied by BASF; toluylene-2,4- and toluylene-2,6-diisocyanate mixture) are then added immediately and after 6 seconds the mixture is poured into a lined mould and the exothermic temperature is measured during foaming to a foam block. The foam blocks are cooled for 24 hours in a climatic chamber at 5° C. and stored. 2 cm slices are sawed from the center of the blocks and round (cylindrical) test samples are cut therefrom using a boring tool. The samples are aged in a test tube in the presence of air at room temperature and 200° C. for 30 minutes in a preheated alu-block thermostat (dynamic heat test). The yellowing of these test samples is determined as Yellowness Index (YI) according to ASTM D-1925-77. Low YI values denote little discoloration, high YI values severe discoloration of the samples. The results are summarized in Tables 7 and 8.

TABLE 7

| Example | Concentration of stabilizers in % (by weight) | YI room temp. | YI 200° C. |
|---|---|---|---|
| 7a[i)] | — | 1.0 | 72.0 |
| 7b[k)] | 0.15% Compound (301) 0.15% Irganox ® 5057[c)] | 0.5 | 3.0 |
| 7c[k)] | 0.15% Compound (302) 0.15% Irganox ® 5057[c)] | 0.5 | 3.0 |
| 7d[k)] | 0.15% Compound (318) 0.15% Irganox ® 5057[c)] | 0.5 | 3.0 |

TABLE 8

| Example | Concentration of stabilizers in % (by weight) | YI room temp. | YI 200° C. |
|---|---|---|---|
| 7e[i)] | — | 0.6 | 70.0 |
| 7f[k)] | 0.10% Compound (301) 0.10% Irganox ® 5057[c)] 0.10% Irganox ® 1135[d)] | 0.3 | 2.7 |
| 7g[k)] | 0.10% Compound (302) 0.10% Irganox ® 5057[c)] 0.10% Irganox ® 1135[d)] | 0.3 | 2.7 |
| 7h[k)] | 0.10% Compound (318) 0.10% Irganox ® 5057[c)] 0.10% Irganox ® 1135[d)] | 0.3 | 2.7 |

For footnotes [c)], [d)], [i)] and [k)] see the end of Table 21.

EXAMPLE 8

Stabilizing polypropylene fibers processed at 300° C.

2.0 kg of polypropylene powder (B 10 FB® from Polychim S.A., France), which has a melt index of 12.0 g/dmin measured in accordance with DIN 53735 at 230° C. under 2.16 kg, is homogenized with 0.05% of calcium stearate and with the stabilizers indicated in Tables 9 and 10 for 2 minutes in a high-speed mixer. This mixture is extruded at 60 revolutions per minute in an extruder having a barrel diameter of 20 mm and a length of 400 mm, the three heating zones being set at the following temperatures: 200, 220 and 220° C. The extrudate is passed through a water bath for cooling and then granulated. These granules are processed to give a multifilament fiber. This is done using a single-screw extruder with a melt pump and a 37-hole spinning head. The maximum processing temperature is 300° C.

A portion of the unstretched fiber thus obtained is pressed for 6 minutes at 230° C. to form a sheet with a thickness of 2 mm. The melt index (MFI, melt flow index) of this sheet is measured in accordance with DIN 53735 at 230° C. and 2.16 kg. A large increase in the melt index denotes severe chain degradation and thus poor stabilization. The results are compiled in Table 9.

Another portion of the unstretched fiber thus obtained is treated with a lubricant (Limanol®P 25, Schill und Seilacher, Böblingen, Germany) and subjected to preliminary drawing. This preliminary drawing leads to a fiber strand having a linear density of 416 g/90 m. This means that a fiber strand 90 m in length has a weight of 416 g. In a further operation, this fiber strand is again drawn at 120° C. by a factor of 3.2 using a drawing apparatus. This leads to a fiber strand having a linear density of 130 g/90 m.

A portion of this fiber strand is used to produce a knitted tube. The yellowness index ($YI_1$) of this knitted tube is determined in accordance with ASTM D 1925-77. Low $YI_1$ values denote little discoloration, high $YI_1$ values severe discoloration of the samples. The results are compiled in Table 9. This knitted tube is exposed in the presence of from 4 to 6 ppm nitrogen dioxide ($NO_2$) at 40° C. and 87% relative atmospheric humidity for 48 hours in accordance with AATCC 164. The yellowness index ($YI_2$) of this exposed knitted tube is determined in accordance with ASTM D 1925-77. Low $YI_2$ values denote little discoloration, high $YI_2$ values severe discoloration of the samples. The results are compiled in Table 9.

Another portion of the fiber strand is used to carry out an oven ageing test at 100° C. In this test, a measurement is made, in days, of the time taken for the fiber strand to tear under the test conditions. The longer the period before tearing of the fiber strand, the better the stabilization. The results are compiled in Table 10.

Another portion of the unstretched fiber is pressed for 6 minutes at 230° C. to form a thin film with a thickness of 0.10 mm. This film is subjected to a Xenon test in accordance with DIN 53387. In this test, the film is exposed in a Xenon 1200 weathering apparatus until a carbonyl index of 0.25 is observed in the wavelength range from 1760 to 1680 $cm^{-1}$. The larger the number, the better the stabilization. The results are compiled in Table 10.

TABLE 9

| Example | Stabilizers | $YI_1$ after spinning | $YI_2$ after $NO_2$ exposure | MFI after spinning |
|---|---|---|---|---|
| 8a[i)] | — | 0.3 | 1.4 | 109.0 |
| 8b[k)] | 0.100% Compound (301) 0.050% Tinuvin ® 622[e)] | 1.5 | 5.4 | 34.5 |
| 8c[k)] | 0.100% Compound (301) 0.050% Chimassorb ® 944[f)] | 1.6 | 4.7 | 33.0 |

TABLE 9-continued

| Example | Stabilizers | YI$_1$ after spinning | YI$_2$ after NO$_2$ exposure | MFI after spinning |
|---|---|---|---|---|
| 8d$^{k)}$ | 0.100% Compound (301)<br>0.050% Chimassorb ® 119$^{g)}$ | 0.8 | 4.7 | 31.9 |
| 8e$^{k)}$ | 0.075% Compound (301)<br>0.050% Tinuvin ® 622$^{e)}$<br>0.075% Irgafos ® 168$^{a)}$ | 0.8 | 4.7 | 32.0 |
| 8f$^{k)}$ | 0.075% Compound (301)<br>0.050% Chimassorb ® 944$^{f)}$<br>0.075% Irgafos ® 168$^{a)}$ | 1.5 | 4.8 | 32.9 |
| 8g$^{k)}$ | 0.075% Compound (301)<br>0.050% Chimassorb ® 944$^{f)}$<br>0.075% Irgafos ® 38$^{h)}$ | 1.5 | 4.7 | 31.9 |
| 8h$^{k)}$ | 0.075% Compound (301)<br>0.050% Chimassorb ® 119$^{g)}$<br>0.075% Irgafos ® 168$^{a)}$ | 1.5 | 4.7 | 32.6 |

For footnotes $^{a)}$, $^{e)}$, $^{f)}$, $^{g)}$, $^{h)}$, $^{i)}$ and $^{k)}$ see the end of Table 21.

TABLE 10

| Example | Stabilizers | Oven ageing (days) | Xenon test (hours) |
|---|---|---|---|
| 8a$^{i)}$ | — | 1 | 200 |
| 8c$^{k)}$ | 0.100% Compound (306)<br>0.050% Chimassorb ® 944$^{f)}$ | 39 | 1350 |
| 8d$^{k)}$ | 0.100% Compound (306)<br>0.050% Chimassorb ® 119$^{g)}$ | 39 | 1540 |
| 8f$^{k)}$ | 0.075% Compound (306)<br>0.050% Chimassorb ® 944$^{f)}$<br>0.075% Irgafos ® 168$^{a)}$ | 39 | 1340 |
| 8g$^{k)}$ | 0.075% Compound (306)<br>0.050% Chimassorb ® 944$^{f)}$<br>0.075% Irgafos ® 38$^{h)}$ | 39 | 1360 |
| 8h$^{k)}$ | 0.075% Compound (306)<br>0.050% Chimassorb ® 119$^{g)}$<br>0.075% Irgafos ® 168$^{a)}$ | 39 | 1500 |

For footnotes $^{a)}$, $^{f)}$, $^{g)}$, $^{h)}$, $^{i)}$ and $^{k)}$ see the end of Table 21.

EXAMPLE 9

Preparation of polyolefin hollow articles by the rotomolding process.

100 Parts of low density polyethylene, copolymerized with hexene (PE-LLD), type Quantum® Petrothene® GA-635-661, having a melt flow index of 6.5 g/10 min and a density of 0.935 g/cm$^3$, are mixed with 0.170 part of Chimassorb® 944 [formula see footnote (b) after Table 21], 0.050 part of zinc stearate and the stabilizers cited in Tables 11 and 12 at 232° C. in a Superior/MPM Extruder, fitted with a 24:1 Maddock type L/D screw, at 100 revolutions per minute. The polymer is then ground. The particle size of the polymer is from 150 to 500 μm. Owing to the larger surface of the particles obtained by grinding, the heat can be absorbed faster, which goes hand in hand with a lower energy consumption.

The actual rotomolding process or rotational molding process, which permits the production of fairly large three-dimensional solids, is carried out in a Clamshell type rotomolder FSP M20. In this machine, an aluminium mold, which is mounted on an arm and into which the plastic sample is filled, is heated with a gas burner with circulation of the hot air over 5 minutes to 316° C., or over 6 minutes to 329° C., and is then kept at this temperature for a specific time (see Tables 11 and 12). Subsequently, the oven is opened and the mold is cooled first for 7 minutes with circulating air, then for 7 minutes by spraying with water and finally for another 2 minutes with circulating air. During the entire heating and cooling process, the mold, which is mounted on two axes at right angles to each other, is rotated, the speed of the main axis being kept at 6 revolutions per minute and the rotational ratio being 4.5:1. After cooling, the lid of the mold is opened and the resultant hollow article is taken out. The yellowness index (YI) of the exterior of the molded articles is determined according to ASTM D 1925-70. Low YI values denote little discoloration, high YI values strong discoloration of the samples. The less discoloration, the more effective the stabilizer. The results are summarized in Tables 11 and 12.

TABLE 11

Rotomolding at 316° C.

| | | Yellowness Index after | |
|---|---|---|---|
| Example | Stabilizer | 8 minutes | 10 minutes |
| 9a$^{i)}$ | 0.05% Irganox ® 1010$^{l)}$<br>0.10% Irgafos ® 168$^{a)}$ | 6.3 | 17.8 |
| 9b$^{k)}$ | 0.02% compound (301)<br>0.08% Irgafos ® 168$^{a)}$ | 4.3 | 5.3 |

TABLE 12

Rotomolding at 329° C.

| | | Yellowness Index after | |
|---|---|---|---|
| Example | Stabilizer | 6 minutes | 8 minutes |
| 9c$^{i)}$ | 0.05% Irganox ® 1010$^{l)}$<br>0.10% Irgafos ® 168$^{a)}$ | 4.1 | 16.7 |
| 9d$^{k)}$ | 0.02% compound (301)<br>0.08% Irgafos ® 168$^{a)}$ | 4.1 | 5.8 |

For footnotes $^{a)}$, $^{i)}$, $^{k)}$ and $^{l)}$ see the end of Table 21.

EXAMPLE 10

Stabilisation of polyethylene which is in permanent contact with water.

0.10% by weight of calcium stearate and a stabilizer mixture comprising 0.10% by weight of Irganox®1010 (pentaerythritol tetrakis[3-(3,5-di-tert-butyl-4-hydroxyphenyl)propionate]), 0.05% by weight of Irgafos®68 (tris(2,4-di-tert-butylphenyl)phosphite) and 0.05% by weight of compound (302) (Table 3) is added dry to a polyethylene polymer (Hostalene® CRP 100; PE-HD) taken direct from a reactor and are incorporated therein in a Pappenmaier mixer (type 20) within 2 minutes.

In an extruder, of Schwabenthan, the stabilized polyethylene is homogenised and processed to granulate. For the extraction tests in water, 200 mm by 150 mm by 2 mm test plates are pressed from the granulate of the individual formulations using a table press. To ease the demoulding of the test plates, the pressing process is carried out between two aluminium foils.

The stabilizer extraction tests are carried out with deionised water. Preliminary heating of the extraction vessels is carried out in a circulating air oven, of Heraeus (Hanau, Germany), at a maximum temperature deviation of 1.5° C. Glass vessels are used for extraction tests below the boiling point of water, such as at 80° C. Owing to the risk of oversaturating the water with stabilizers, the amount of liquid used for the tests is fixed at c. 400 ml per c. 70 g of polymer and the water is replaced with fresh water at regular intervals, i.e. whenever a sample is taken.

The test plates are subjected to the above test conditions for 50 days at 80° C. Upon termination of the extraction test, the residual stabilizer content and the oxidation induction time of the test plates are determined.

The residual content of sterically hindered phenol, Irganox®1010, is determined using an internal standard in an HPLC appliance of the Spectra Physics SP 8800 type, equipped with autosampler and UV/VIS detector of the Spectra 200 type. The chromatography is carried out at room temperature using a Hyperchrome 125×4.6 mm type column which is filled with Nucleosil C 185 µm. The injection volume is 14 µl at a flow rate of 1.5 ml/minute. UV detection takes place at 270 nm.

The oxidation induction time which is determined using a "DuPont-instrument 910 Differential Scanning Calorimeter", of TA Instruments (Alzenau, Germany), and taking a 5 to 10 mg amount of sample, describes the time in minutes at constant thermal stress (190° C./$O_2$) up to the start of the complete degradation of the polyethylene sample. The longer the oxidation induction time, the better stabilized the polyethylene and the more stable is the polyethylene against extracting water with which it is in permanent contact. The results show that the stability of polyolefins which are in permanent contact with extracting media is improved if they contain the compound (302) according to the instant invention as stabilizer.

EXAMPLE 11

Measuring the discoloration of powder coatings based on a carboxy-functional polyester and cured in electric and gas ovens.

To prepare the powder coating composition based on a carboxy-functional polyester, components 1 to 6 (formulation without additives) or components 1 to 7 (formulation containing the stabilizers) are employed in the sequence indicated (cf. Table 13).

TABLE 13

| | Examples (amount in grams) | |
|---|---|---|
| Components | 1a | 1b to 1i |
| 1. Crylcoat ® 360[a] | 591 | 591 |
| 2. Araldit ® GT 7004[b] | 394 | 394 |
| 3. Octadecyltrimethylammonium bromide[c] | 3.6 | 3.6 |
| 4. Resiflow ® PV 88[d] | 12 | 12 |
| 5. Benzoin[e] | 3 | 3 |
| 6. Titanium dioxide type R-KB-5[f] | 500 | 500 |
| 7. Stabilizers (see Tables 14 and 15) | — | 6 |
| Total: | 1503.6 | 1509.6 |

[a] Crylcoat ® 360 from UCB S.A., Drogenbos, Belgium.
[b] Araldit ® GT 7004 (Ciba Specialty Chemicals Inc.) is a bisphenol A diglycidyl ether.
[c] Octadecyltrimethylammonium bromide from Fluka AG, Buchs, Switzerland.
[d] Resiflow ® PV 88 from Worlée Chemie GmbH, Lauenburg, Germany.
[e] Benzoin from Fluka AG.
[f] Titanium dioxide type R-KB-5 from Bayer AG, Leverkusen, Germany.

The components weighed out in this way are mixed using a planetary stirrer. The mixture is then extruded on a prism extruder at 300 revolutions/minute and at 100° C. and is rolled out. The powder coating composition is coarsely comminuted using a bench cutter and is ground in a Retsch ZM-1 ultracentrifugal mill with a 0.75 mm annular-perforation screen at 15,000 revolutions/minute. Finally, the powder is passed through a 30 µm screen on a centrifugal screening machine.

The finished powder coating composition is sprayed electrostatically to a coat thickness of 70 µm onto aluminium panels using an ESB-Wagner corona cup gun at 60 kV. Some of the coated panels are cured at 180° C. for 90 minutes in an electric oven. The remaining coated panels are cured at 180° C. for 45 minutes in a gas oven with an $NO_2$ content of 20 ppm. The yellowness index (YI) of the samples is determined in accordance with ASTM D 1925-70. Low YI values denote little discoloration, high YI values denote severe discoloration of the samples. The less the discoloration, the more effective the stabilizer. The results are summarized in Tables 14 and 15.

TABLE 14

Curing for 90 minutes in an electric oven at 180° C.

| Example | Stabilizers (% rel. to components 1 to 5) | Yellowness index after 90 minutes (ASTM D 1925-70) |
|---|---|---|
| 11a[i] | — | 3.1 |
| 11b[k] | 0.60% Compound (301) | 2.8 |
| 11c[k] | 0.50% Irgafos ® 168[a] 0.10% Compound (301) | 2.8 |
| 11d[k] | 0.15% Irgafos ® 168[a] 0.15% HALS mixture[m] 0.30% Compound (301) | 2.8 |
| 11e[k] | 0.15% lrgafos ® 168[a] 0.15% Irganox ® 1010[l] 0.30% Compound (301) | 2.8 |

For footnotes [a], [i], [k], [m] and [l] see the end of Table 21.

TABLE 15

Curing for 45 minutes in a gas oven at 180° C.

| Example | Stabilizers (% rel. to components 1 to 5) | Yellowness index after 90 minutes (ASTM D 1925-70) |
|---|---|---|
| 11f[i] | — | 4.2 |
| 11g[k] | 0.60% Compound (301) | 3.5 |
| 11h[k] | 0.50% Irgafos ® 168[a] 0.10% Compound (301) | 3.5 |
| 11i[k] | 0.15% Irgafos ® 168[a] 0.15% HALS mixture[m] 0.30% Compound (301) | 3.4 |

For footnotes [a], [m], [k] and [l] see the end of Table 21.

EXAMPLE 12

Stabilizing polypropylene in the case of multiple extrusion and at especially high temperatures.

1.5 kg of polypropylene powder (Profax®6501), which has been initially stabilized with 0.008% of Irganox®1076 (n-octadecyl 3-[3,5-di-tert-butyl-4-hydroxyphenyl] propionate) (with a melt index of 3.2 measured at 230° C. and under 2.16 kg), are mixed with 0.10% of calcium stearate and 0.015 to 0.20% of the stabilizers listed in Table 16. This mixture is extruded in an extruder having a barrel diameter of 20 mm and a length of 400 mm at 100 revolutions per minute, the maximum extruder temperature being set at 280, 300, 320 and 340° C. For cooling, the extrudate is drawn through a water bath and then granulated. These granules are extruded repeatedly. After 5 extrusions, the melt index is measured (at 230° C. under 2.16 kg). A large increase in the melt index denotes severe chain breakdown and hence poor stabilization. The results are summarized in Table 16.

TABLE 16

| Example | Stabilizers | Amount (% by wt.) | Melt index after 5 extrusions |
|---|---|---|---|
| 12a[i] | Irgafos ® 168[a] | 0.10 | 18.4 |
| | Irganox ® 1010[l] | 0.10 | |
| | Chimassorb ® 944[f] | 0.20 | |
| 12b[k] | Compound (302) | 0.015 | 8.9 |
| | Irgafos ® 168[a] | 0.10 | |
| | Irganox ® 1010[l] | 0.05 | |
| | Chimassorb ® 944[f] | 0.10 | |
| 12c[k] | Compound (302) | 0.015 | 8.7 |
| | Irgafos ® 168[a] | 0.10 | |
| | Irganox ® 1010[l] | 0.05 | |
| | Chimassorb ® 119[g] | 0.10 | |

For footnotes [a], [f], [g], [i], [k] and [l] see the end of Table 21.

EXAMPLE 13

Stabilization of polycarbonate.

1.0 kg of a polycarbonate powder which has been dried for 8 hours at 120° C. in a vacuum drying oven (Lexan®115, of General Electric) and 0.1 to 0.6 g (0.01 to 0.06%) of the stabilizers listed in Table 17 are mixed for 2 minutes in a Henschel mixer. This mixture is then extruded in a Schwabenthan extruder at a maximum of 280° C. The polymer string is then granulated. Using an injection moulding machine, plates having a layer thickness of 2 mm are then moulded from the granulate so obtained at a maximum of 300° C. These plates are then aged in a circulating air oven at 135° C. for 2000 hours. The yellowness index (YI) of these plates is then determined according to ASTM D 1925-70 and the transmission is determined in percent at 450 nm. Low YI values denote little discoloration, high YI values high discoloration of the patterns. The less discoloration, the more effective the stabilizer. The higher the transmission values, the more effective the stabilizer. The results are compiled in Tables 17 and 18.

TABLE 17

| Example | Stabilizers | Yellowness index prior to oven-ageing | Yellowness index after 2000 hours at 135° C. |
|---|---|---|---|
| 13a[i] | — | 4.1 | 25.5 |
| 13b[i] | 0.05% Irgafos ® 168[a] | 3.5 | 23.9 |
| 13c[k] | 0.01% Compound (301) | 3.5 | 16.6 |
| 13d[k] | 0.01% Compound (314) | 3.5 | 15.5 |
| 13e[k] | 0.05% Irgafos ® 168[a] 0.01% compound (301) | 3.4 | 15.3 |
| 13f[k] | 0.05% Irgafos ® 168[a] 0.01% compound (314) | 3.4 | 15.0 |

TABLE 18

| Example | Stabilizers | Transmission in % prior to oven-aging | Transmission in % after 2000 hours at 135° C. |
|---|---|---|---|
| 13a[i] | — | 84.8 | 76.2 |
| 13b[i] | 0.05% Irgafos ® 168[a] | 84.8 | 77.9 |
| 13c[k] | 0.01% Compound (301) | 85.9 | 81.2 |
| 13d[k] | 0.01% Compound (314) | 85.9 | 81.5 |
| 13e[k] | 0.05% Irgafos ® 168[a] 0.01% Compound (301) | 85.9 | 81.4 |

TABLE 18-continued

| Example | Stabilizers | Transmission in % prior to oven-aging | Transmission in % after 2000 hours at 135° C. |
|---|---|---|---|
| 13f[k] | 0.05% Irgafos ® 168[a] 0.01% compound (314) | 86.0 | 81.4 |

For footnotes [a], [i] and [k] see the end of Table 21.

EXAMPLE 14

Stabilization of polycarbonate.

1.0 kg of a polycarbonate powder which has been dried for 8 hours at 120° C. in a vacuum drying oven (Lexan®145, of General Electric) is charged with the stabilizers listed in Table 19 and is mixed for 2 minutes in a Henschel mixer. This mixture is then extruded in a Schwabenthan extruder at a maximum of 280° C. The polymer string is then granulated. Using an injection moulding machine, plates having a layer thickness of 2 mm are then moulded from the granulate so obtained at a maximum of 300° C. These plates are then aged in a circulating air oven at 135° C., the time in hours until the yellowness index (YI) reaches a value of 20 according to ASTM D 1925-70 being measured. The longer the time, the more effective the stabilizer. The results are compiled in Table 19.

TABLE 19

| Example | Stabilizers | Time in hours at 135° C. to YI = 20 |
|---|---|---|
| 14a[i] | — | 1570 |
| 14b[i] | 0.05% Irgafos ® 168[a] | 2010 |
| 14c[k] | 0.006% Compound (308) 0.022% Irgafos ® 168[a] 0.012% Irganox ® 1076[n] | 2350 |
| 14d[k] | 0.009% Compound (308) 0.034% Irgafos ® 168[a] 0.017% Irganox ® 1076[n] | 2355 |

For footnotes [a], [i], [k] and [n] see the end of Table 21.

EXAMPLE 15

Stabilization of polyesters.

2.5 kg of a polyester which has been dried for 12 hours at 120° C. in a vacuum drying oven (Polyclear® T86, of Hoechst) is charged with the stabilizers listed in Table 20 and is mixed for 2 hours in a Henschel mixer. This mixture is then extruded in a Schwabenthan extruder at a maximum of 275° C. The polymer string is then granulated. The granulate so obtained is dried for another 12 hours in a vacuum drying oven. In a double determination, 500 mg of the granulate is heated over 10 minutes to 290° C. and is stored for 1 hour under pure oxygen in a rancimate at 290° C. The resulting gaseous separation products are continuously led into an aqueous collecting solution and the conductivity ($\mu$S) of this solution is continuously measured. Low conductivity values signify that few separation products are formed, high conductivity values signify that very many separation products are formed. The lower the conductivity values, the more effective the stabilizer. The results are compiled in Table 20.

TABLE 20

| Example | Stabilizers | Conductivity ($\mu$S) |
|---|---|---|
| 15a[i] | — | 46 |
| 15b[k] | 0.20% Compound (302) | 33 |

For footnotes [i] and [k] see the end of Table 21.

EXAMPLE 16

Stabilization of light-colored SBR-vulcanisate (ozone atmosphere for 48 hours).

100 parts by weight of Cariflex®S-1502 (styrene/butadiene rubber, Shell) are processed at 60° C., in a mixing mill, with 30.0 parts by weight of Kronos®CL 220 [titanium dioxide (pigment), Kronos Titan GmbH], 30.0 parts by weight of Aktisil®MM [kaolin (filler), Hoffmann Mineral, Neuburg/Donau], 5.0 parts by weight of Naftolen®N 401 [plasticizer, Metaligesellschaft], 10.0 parts by weight of zinc oxide [vulcanization activator], 2.0 parts by weight of stearic acid [vulcanization activator], 2.0 parts by weight of sulfur [vulcanizing agent], 1.0 part by weight of Vulkacit®MOZ [vulcanisation accelerator, Bayer], 0.25 part by weight of Vulkacit®Thiuram [vulcanization accelerator, Bayer] and 1.0 part by weight of the stabilizer to be tested according to Table 24, to form a homogeneous mixture, the vulcanization system (sulfur, Vulkacit®MOZ and Vulkacit®Thiuram) not being added until the end of the mixing process. The mixture is vulcanized in electrical vulcanization presses at 150° C. until T95 is reached in the rheometer curves to form elastomer plates 2 mm thick, 21 cm long and 8.0 cm wide.

Some of the elastomer plates so obtained are tested for the action of ozone according to the ASTM standard D 3395-86 while subject to dynamic elongation. In this test, the plates are first stored for 30 days in a standard atmosphere [23/50 SN-ISO 291]. Test specimens measuring 20 cm by 1 cm are then punched out and exposed to an ozone atmosphere for 48 hours (ozone content: 50 pphm; temperature: 40° C.; humidity: 50% rel.; elongation: 0 to 25%; elongation rate: 0.5 Hz; number of load cycles: approximately 173 000). The test plates are then assessed for crack formation according to ASTM D 3395-86. Grade 0 denotes no cracks; grade 1 denotes narrow flat cracks; grade 2 denotes moderately broad, moderately deep cracks, clearly visible; grade 3 denotes broad and deep cracks. The lower the grade number, the better the stabilization of the elastomer plates. The results are compiled in Table 21.

The remaining elastomer plates are stored for 3 weeks at room temperature in a standard laboratory atmosphere in diffuse daylight. The ΔL-color of those plates is then determined according to DIN 6167, which corresponds to a scale of from 0 to 100. No discoloration is indicated by a value of 100. The results are compiled in Table 21.

TABLE 21

| Example | Stabilizer | Crack formation according to ASTM D 3395-86 | ΔL-color according to DIN 6167 |
|---|---|---|---|
| 16a[i] | — | grade 1–2 | 94 |
| 16b[i] | 1.0 phr[n] Vulkanox ® 4010[t] | grade 0 | 70 |
| 16c[k] | 1.0 phr[n] Compound (301) | grade 0–1 | 94 | a) Irgafos®168 (Ciba Specialty Chemicals Inc.) is tris(2,4-di-tert-butylphenyl)phosphite.

b) Sandostab®P-EPQ (Clariant) is tetrakis(2,4-di-tert-butylphenyl)-4,4'-biphenylene diphosphonite.

c) Irganox®5057 (Ciba Specialty Chemicals Inc.) is a secondary amine antioxidant and is a technical mixture, obtained by reaction of diphenylamine with diisobutylene, comprising
   a') 3% of diphenylamine;
   b') 14% of 4-tert-butyldiphenylamine;
   c') 30% of compounds of the group
      i) 4-tert-octyldiphenylamine,
      ii) 4,4'-di-tert-butyldiphenylamine,
      iii) 2,4,4'-tris-tert-butyldiphenylamine;
   d') 29% of the compounds of the group
      i) 4-tert-butyl-4'-tert-octyldiphenylamine,
      ii) o,o'-, m,m'- or p,p'-di-tert-octyldiphenylamine,
      iii) 2,4-di-tert-butyl-4'-tert-octyldiphenylamine;
   e') 24% of the compounds of the group
      i) 4,4'-di-tert-octyldiphenylamine and
      ii) 2,4-di-tert-octyl-4'-tert-butyldiphenylamine.

d) Irganox®1135 (Ciba Specialty Chemicals Inc.) is a phenolic antioxidant of the formula A-1.

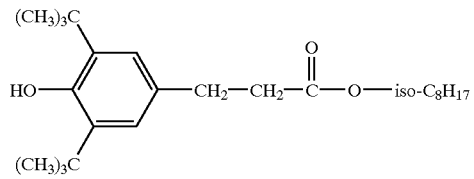

(A-1)

e) Tinuvin®622 (Ciba Specialty Chemicals Inc.) is a compound of the formula H1 in which the average molecular weight is about 3000.

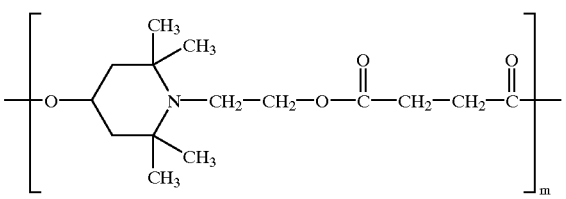

(H1)

f) Chimassorb®944 (Ciba Specialty Chemicals Inc.) denotes linear or cyclic condensation products prepared from N,N'-bis(2,2,6,6-tetramethyl-4-piperidyl)hexamethylendiamine and 4-tert-octylamino-2,6-dichloro-1,3,5-triazine and is a compound of the formula H2 in which the average molecular weight is about 2500.

(H2)

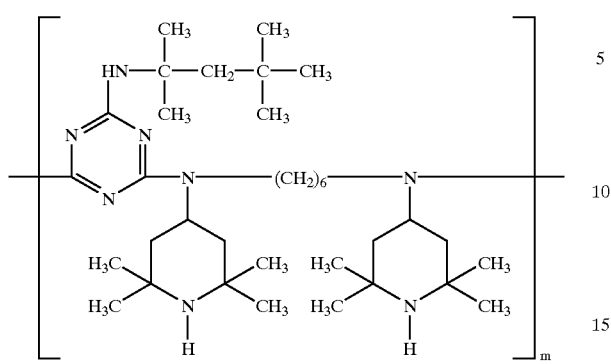

g) Chimassorb®119 (Ciba Specialty Chemicals Inc.) denotes condensation products prepared from 2-chloro-4,6-di(4-n-butylamino-1,2,2,6,6-pentamethylpiperidyl)-1,3,5-triazine and 1,2-bis(3-aminopropylamino)ethane and is a compound of the formula H3

(H3)

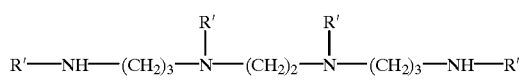

in which

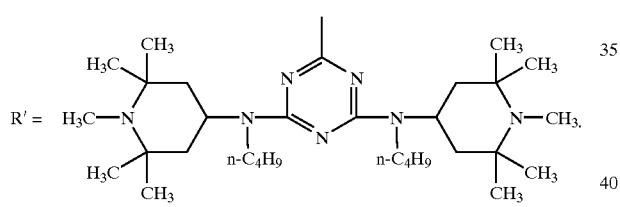

h) Irgafos®38 (Ciba Specialty Chemicals Inc.) is a compound of the formula P-1.

(P-1)

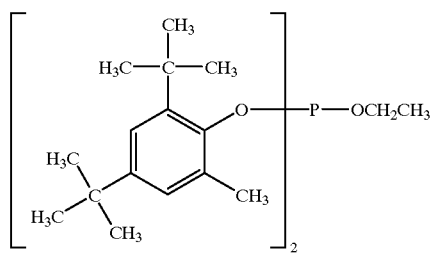

i) Comparison Example.
k) Example of this invention.
l) Irganox®1010 (Ciba Specialty Chemicals Inc.) denotes the pentaerythritol ester of 3-(3,5-di-tert-butyl-4-hydroxyphenyl)propionic acid.
m) HALS mixture is a 1:1 mixture of Tinuvin®622 [Ciba Specialty Chemicals Inc.; see footnote e)] and Chimassorb®119 (Ciba Specialty Chemicals Inc.; see footnote g)].

n) Irganox®1076 (Ciba Specialty Chemicals Inc.) denotes a compound of formula A-2.

(A-2)

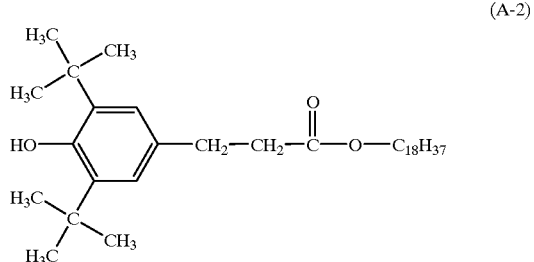

t) Vulkanox®4010 (Bayer) denotes 4-isopropylaminodiphenylamine of formula A.

(A)

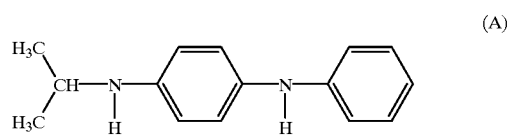

u) phr denotes "parts per hundred of rubber".

What is claimed is:

1. A process for the preparation of compounds of formula I (I)

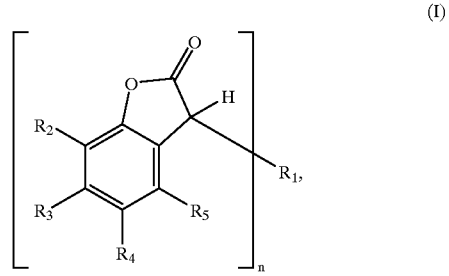

wherein, when n is 1, $R_1$ is naphthyl, phenanthryl, anthryl, 5,6,7,8-tetrahydro-2-naphthyl, thienyl, benzo[b]thienyl, naphtho[2,3-b]thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyridyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$–$C_{18}$alkyl, $C_1$–$C_{18}$alkoxy, $C_1$–$C_{18}$alkylthio, di-($C_1$–$C_4$alkyl)amino, phenyl, benzyl, benzoyl or by benzoyloxy or $R_1$ is a radical of formula II or III (II)

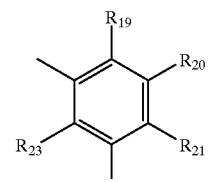

(III)

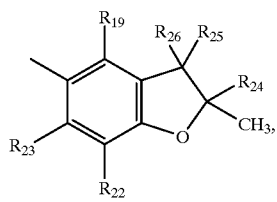

when n is 2,

R₁ is phenylene or naphthylene each unsubstituted or substituted by $C_1$–$C_4$alkyl or by fluorine; or is —R₆—X—R₇—, R₂, R₃, R₄ and R₅ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals R₂ and R₃ or the radicals R₃ and R₄ or the radicals R₄ and R₅, together with the carbon atoms to which they are bonded, form a benzo ring, R₄ is additionally —(CH₂)$_p$—COR₉ or —(CH₂)$_q$OH or, when R₃ and R₅ are hydrogen, R₄ is additionally a radical of formula IV (IV)

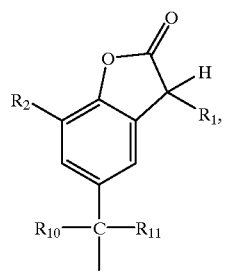

wherein R₁ is as defined above for the case where n=1,

R₆ and R₇ are each independently of the other phenylene or naphthylene each unsubstituted or substituted by $C_1$–$C_4$alkyl, R₈ is $C_1$–$C_8$alkyl, R₉ is hydroxy,

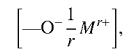

$C_1$–$C_{18}$alkoxy or

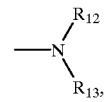

R₁₀ and R₁₁ are each independently of the other hydrogen, CF₃, $C_1$–$C_{12}$alkyl or phenyl, or R₁₀ and R₁₁, together with the carbon atom to which they are bonded, form a $C_5$–$C_8$cycloalkylidene ring unsubstituted or substituted by from 1 to 3 $C_1$–$C_4$alkyl groups;

R₁₂ and R₁₃ are each independently of the other hydrogen or $C_1$–$C_{18}$alkyl, R₁₄ is hydrogen or $C_1$–$C_{18}$alkyl, R₁₉, R₂₀, R₂₁, R₂₂ and R₂₃ are each independently of the others hydrogen, halogen, fluoro-substituted $C_1$–$C_{12}$alkyl; —CN,

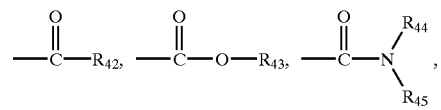

—SOR₄₆, —SO₂R₄₆, —SO₃R₄₆, —SO₂R₄₆, SO₃R₄₆, hydroxy, $C_1$–$C_{25}$alkyl; $C_2$–$C_{25}$alkyl interrupted by oxygen, sulfur or by

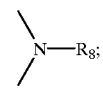

$C_1$–$C_{25}$alkoxy; $C_2$–$C_{25}$alkoxy interrupted by oxygen, sulfur or by

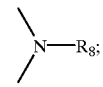

$C_1$–$C_{25}$alkylthio, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy; di($C_1$–$C_4$alkyl)amino, $C_1$–$C_{25}$alkanoyl; $C_3$–$C_{25}$alkanoyl interrupted by oxygen, sulfur or by

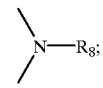

$C_1$–$C_{25}$alkanoyloxy; $C_3$–$C_{25}$alkanoyloxy interrupted by oxygen, sulfur or by

$C_1$–$C_{25}$alkanoylamino, $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

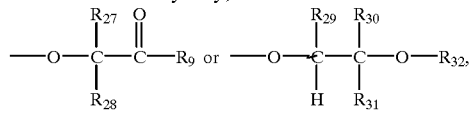

$R_{24}$ is hydrogen, $C_1$–$C_4$alkyl, or unsubstituted or $C_1$–$C_4$alkyl-substituted phenyl, $R_{25}$ and $R_{26}$ are hydrogen, $C_1$–$C_4$alkyl or phenyl, with the proviso that at least one of the radicals $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl; $C_2$–$C_{25}$alkyl interrupted by oxygen, sulfur or by

$C_7$–$C_9$phenylalkyl unsubstituted or substituted on the phenyl radical by from 1 to 3 $C_1$–$C_4$alkyl groups; or $C_7$–$C_{25}$phenylalkyl interrupted by oxygen, sulfur or by

and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl; $C_3$–$C_{25}$alkanoyl interrupted by oxygen, sulfur or by

$C_2$–$C_{25}$alkanoyl substituted by a di($C_1$–$C_6$alkyl) phosphonate group; $C_6$–$C_9$-cycloalkylcarbonyl, thenoyl, furoyl, benzoyl or $C_1$–$C_{12}$alkyl-substituted benzoyl;

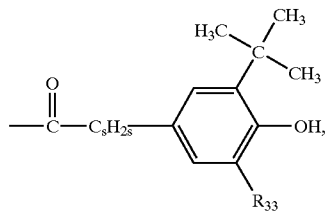

-continued

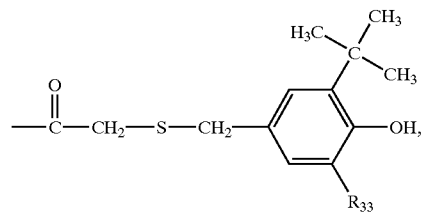

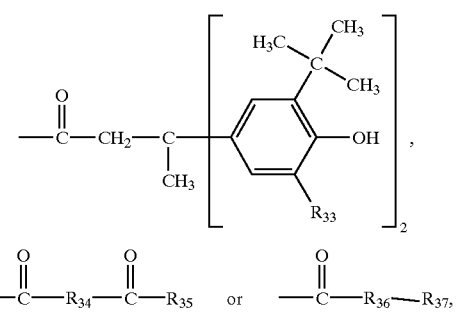

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

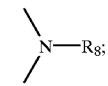

$C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

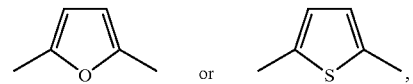

$R_{35}$ is hydroxy,

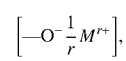

$C_1$–$C_{18}$alkoxy or

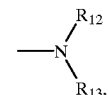

$R_{36}$ is oxygen, —NH— or

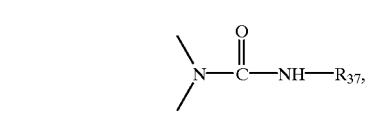

$R_{37}$ is $C_1$–$C_{18}$alkyl or phenyl,
$R_{42}$ is hydrogen, hydroxy,

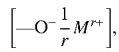

$C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

$R_{43}$ is $C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

$R_{44}$ and $R_{45}$ are each independently of one another hydrogen, $C_1$–$C_{25}$alkyl, hydroxyl-substituted $C_2$–$C_{24}$alkyl; $C_3$–$C_{25}$alkyl which is interrupted by oxygen, sulfur or

$C_7$–$C_9$-phenylalkyl which is unsubstituted or is substituted on the phenyl ring by $C_1$–$C_4$alkyl; or $C_3$–$C_{24}$alkenyl; or $R_{44}$ and $R_{45}$, together with the nitrogen atom to which they are attached, form a 5-, 6- or 7-membered heterocyclic ring which is unsubstituted or is substituted by $C_1$–$C_4$alkyl or is interrupted by oxygen, sulfur or

$R_{46}$ is hydrogen or $C_1$–$C_{25}$alkyl,
M is an r-valent metal cation,
X is a direct bond, oxygen, sulfur or —$NR_{14}$—,
n is 1 or 2,
p is 0, 1 or 2,
q is 1, 2, 3, 4, 5 or 6,
r is 1, 2 or 3, and
s is 0, 1 or 2,
which process comprises hydrolyzing a compound of formula V

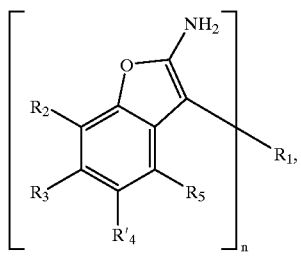

(V)

wherein
$R_1$ and n are as defined above,
$R_2$, $R_3$, $R'_4$ and $R_5$ are each independently of the others hydrogen, fluorine, hydroxy, $C_1$–$C_{25}$alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$-cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R'_4$ or the radicals $R'_4$ and $R_5$, together with the carbon atoms to which they are bonded, form a benzo ring, $R'_4$ is additionally —$(CH_2)_p$—$COR_9$ or —$(CH_2)_q$OH or, when $R_3$ and $R_5$ are hydrogen, $R'_4$ is additionally a radical of formula VI

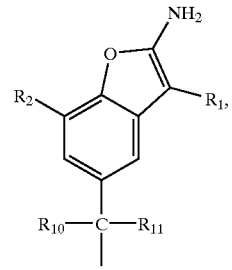

(VI)

wherein $R_1$ is as defined above for the case where n=1, in an aqueous solvent in the presence of an acid.

2. A process according to claim 1, wherein, when n is 2, $R_1$ is phenylene or —$R_6$—X—$R_7$—,
$R_6$ and $R_7$ are phenylene,
X is oxygen or —$NR_{14}$—, and
$R_{14}$ is $C_1$–$C_4$alkyl.

3. A process according to claim 1, wherein
$R_{19}$, $R_{20}$, $R_{21}$, $R_{22}$ and $R_{23}$ are each independently of the others hydrogen, chloro, bromo, fluoro-substituted $C_1$–$C_{12}$alkyl; —CN,

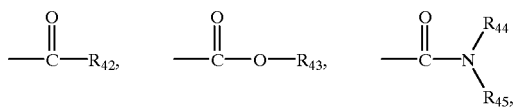

—$SOR_{46}$, —$SO_2R_{46}$, $SO_3R_{46}$, hydroxy, $C_1$–$C_{18}$alkyl; $C_2$–$C_{18}$alkyl interrupted by oxygen or by sulfur; $C_1$–$C_{18}$alkoxy; $C_2$–$C_{18}$alkoxy interrupted by oxygen or by sulfur; $C_1$–$C_{18}$alkylthio, $C_7$–$C_9$phenylalkyl, $C_7$–$C_9$phenylalkoxy, unsubstituted or $C_1$–$C_4$alkyl substituted phenyl; phenoxy, cyclohexyl, $C_5$–$C_8$cycloalkoxy, di($C_1$–$C_4$alkyl)amino, $C_1$–$C_{12}$alkanoyl; $C_3$–$C_{12}$alkanoyl interrupted by oxygen or by sulfur; $C_1$–$C_{12}$alkanoyloxy; $C_3$–$C_{12}$alkanoyloxy interrupted by oxygen or by sulfur; $C_1$–$C_{12}$alkanoylamino, cyclohexylcarbonyl, cyclohexylcarbonyloxy, benzoyl or $C_1$–$C_4$alkyl-substituted benzoyl; benzoyloxy or $C_1$–$C_4$alkyl-substituted benzoyloxy;

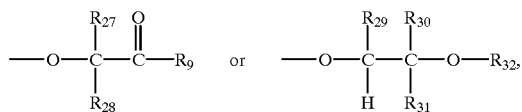

$R_{24}$ is hydrogen or $C_1$–$C_4$alkyl, $R_{25}$ and $R_{26}$ are hydrogen or $C_1$–$C_4$alkyl, with the proviso that at least one of the radicals $R_{25}$ and $R_{26}$ is hydrogen, $R_{27}$ and $R_{28}$ are each independently of the other hydrogen or $C_1$–$C_4$alkyl, $R_{29}$ is hydrogen, $R_{30}$ is hydrogen, phenyl, $C_1$–$C_{18}$alkyl; $C_2$–$C_{18}$alkyl interrupted by oxygen or by sulfur; $C_7$–$C_9$-phenylalkyl; or $C_7$–$C_{18}$phenylalkyl interrupted by oxygen or by sulfur and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{18}$alkanoyl; $C_3$–$C_{12}$alkanoyl interrupted by oxygen or by sulfur; $C_2$–$C_{12}$-alkanoyl substituted by a di($C_1$–$C_6$alkyl) phosphonate group; $C_6$–$C_9$cycloalkylcarbonyl, benzoyl,

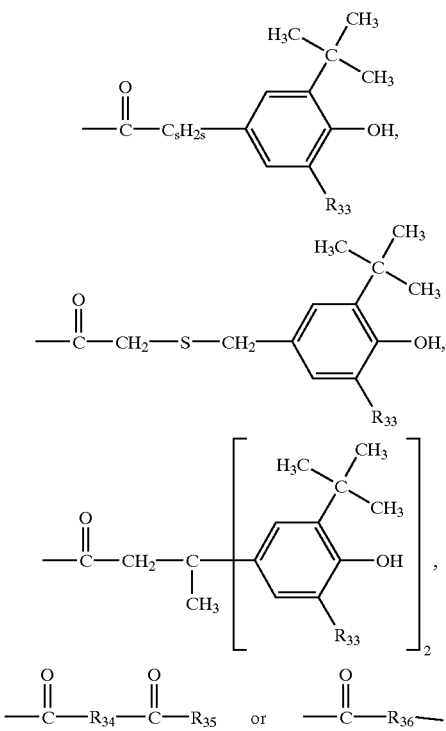

$R_{33}$ is hydrogen or $C_1$–$C_4$alkyl, $R_{34}$ is $C_1$–$C_{12}$alkylene, $C_2$–$C_8$alkylidene, $C_7$–$C_{12}$phenylalkylidene, $C_5$–$C_8$cycloalkylene or phenylene, $R_{35}$ is hydroxy,

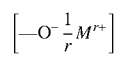

or $C_1$–$C_{18}$alkoxy, $R_{36}$ is oxygen or —NH—, $R_{37}$ is $C_1$–$C_8$alkyl or phenyl, $R_{42}$ is hydrogen, hydroxy, $C_1$–$C_{18}$alkyl, $C_7$–$C_9$phenylalkyl, unsubstituted or $C_1$–$C_4$alkyl-substituted phenyl; $C_5$–$C_8$cycloalkyl; or $C_3$–$C_{25}$alkyl which is interrupted by oxygen or sulfur, $R_{43}$ is $C_1$–$C_{18}$alkyl, $C_7$–$C_9$phenylalkyl, unsubstituted or $C_1$–$C_4$alkyl-substituted phenyl; $C_5$–$C_8$cycloalkyl; or $C_3$–$C_{18}$alkyl which is interrupted by oxygen or sulfur, $R_{44}$ and $R_{45}$ are each independently of one another hydrogen, $C_1$–$C_{18}$alkyl, hydroxyl-substituted $C_2$–$C_{18}$alkyl; $C_3$–$C_{18}$alkyl which is interrupted by oxygen or sulfur; $C_7$–$C_9$-phenylalkyl, or $C_3$–$C_{18}$alkenyl; or $R_{44}$ and $R_{45}$, together with the nitrogen atom to which they are attached, form a 6-membered heterocyclic ring, $R_{46}$ is $C_1$–$C_{18}$alkyl, and s is 1 or 2.

4. A process according to claim 1, wherein, when n is 1, $R_1$ is naphthyl, phenanthryl, thienyl, pyridyl, dibenzofuryl, unsubstituted or $C_1$–$C_4$alkyl-substituted carbazolyl; or fluorenyl, or $R_1$ is a radical of formula II

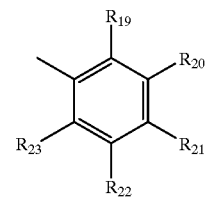

(II)

when n is 2, $R_1$ is phenylene or naphthylene;

$R_{19}$, $R_{20}$, $R_{21}$, $R_{22}$ and $R_{23}$ are each independently of the others hydrogen, chloro, bromo, fluoro-substituted $C_1$–$C_8$alkyl; —CN,

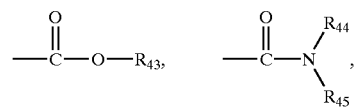

hydroxy, $C_1$–$C_{18}$alkyl, $C_1$–$C_{18}$alkoxy, $C_1$–$C_{18}$alkylthio, phenyl, benzoyl, benzoyloxy or

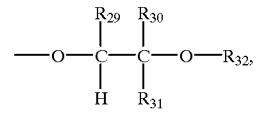

$R_{29}$ is hydrogen, $R_{30}$ is hydrogen, phenyl or $C_1$–$C_{18}$alkyl, $R_{31}$ is hydrogen or $C_1$–$C_4$alkyl, $R_{32}$ is hydrogen, $C_1$–$C_{12}$alkanoyl or benzoyl, and $R_{43}$ is $C_1$–$C_{18}$alkyl, benzyl, phenyl; cyclohexyl; or $C_3$–$C_{12}$alkyl which is interrupted by oxygen, and $R_{44}$ and $R_{45}$ are each independently of one another hydrogen, $C_1$–$C_{14}$alkyl, hydroxyl-substituted $C_2$–$C_{14}$alkyl; $C_3$–$C_{12}$alkyl which is interrupted by oxygen; benzyl or $C_3$–$C_{12}$alkenyl.

5. A process according to claim 4, wherein $R_{19}$ is hydrogen, hydroxy, bromo, trifluoromethyl, $C_1$–$C_4$alkyl or $C_1$–$C_4$alkoxy, $R_{20}$ is hydrogen, bromo, trifluoromethyl, $C_1$–$C_4$alkyl or $C_1$–$C_4$alkoxy, $R_{21}$ is hydrogen, bromo, trifluoromethyl, $C_1$–$C_4$alkyl, $C_1$–$C_4$alkoxy, $C_1$–$C_4$alkylthio, $R_{22}$ is hydrogen, bromo, trifluoromethyl, $C_1$–$C_4$alkyl or $C_1$–$C_4$alkoxy, and $R_{23}$ is hydrogen, hydroxy, bromo, trifluoromethyl, $C_1$–$C_4$alkyl or $C_1$–$C_4$alkoxy.

6. A process according to claim 1, wherein $R_2$, $R_3$, $R_4$ and $R_5$ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; $C_1$–$C_{12}$alkoxy, $C_1$–$C_{12}$alkylthio, $C_1$–$C_4$alkylamino, di-($C_1$–$C_4$alkyl) amino, $C_1$–$C_{18}$alkanoyloxy, $C_1$–$C_{18}$alkanoylamino; $C_3$–$C_{18}$alkanoyloxy interrupted by oxygen, sulfur or by

$C_6$–$C_9$cycloalkylcarbonyloxy, benzoyloxy or $C_1$–$C_8$alkyl-substituted benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —(CH$_2$)$_p$—COR$_9$ or —(CH$_2$)$_q$OH or, when $R_3$ and $R_5$ are hydrogen, $R_4$ is additionally a radical of formula IV

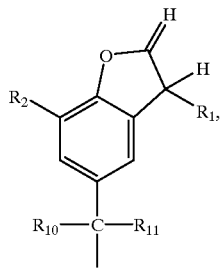

(IV)

$R_8$ is $C_1$–$C_6$alkyl, $R_9$ is hydroxy, $C_1$–$C_{18}$alkoxy or

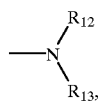

$R_{10}$ and $R_{11}$ are methyl groups or, together with the carbon atom to which they are bonded, form a $C_5$–$C_8$cycloalkylidene ring unsubstituted or substituted by from 1 to 3 $C_1$–$C_4$alkyl groups;

$R_{12}$ and $R_{13}$ are each independently of the other hydrogen or $C_1$–$C_8$alkyl, and q is 2, 3, 4, 5 or 6.

7. A process according to claim 1, wherein at least two of the radicals $R_2$, $R_3$, $R_4$ and $R_5$ are hydrogen.

8. A process according to claim 1, wherein $R_3$ and $R_5$ are hydrogen.

9. A process according to claim 1, wherein $R_2$, $R_3$, $R_4$ and $R_5$ are each independently of the others hydrogen, fluorine, hydroxy, $C_1$–$C_{18}$-alkyl, $C_7$–$C_9$phenylalkyl, phenyl, $C_5$–$C_8$cycloalkyl, $C_1$–$C_6$alkoxy, cyclohexylcarbonyloxy or benzoyloxy, or furthermore the radicals $R_2$ and $R_3$ or the radicals $R_3$ and $R_4$ or the radicals $R_4$ and $R_5$, together with the carbon atoms to which they are bonded, form a benzo ring, $R_4$ is additionally —(CH$_2$)$_p$—COR$_9$, or, when $R_3$ and $R_5$ are hydrogen, $R_4$ is additionally a radical of formula IV, $R_9$ is hydroxy or $C_1$–$C_{18}$alkoxy, and $R_{10}$ and $R_{11}$ are methyl groups or, together with the carbon atom to which they are bonded, form a $C_5$–$C_8$cycloalkylidene ring.

10. A process according to claim 1, wherein $R_2$ is $C_1$–$C_{18}$alkyl or cyclohexyl, $R_3$ is hydrogen, $R_4$ is $C_1$–$C_4$alkyl, cyclohexyl, —(CH$_2$)$_p$—COR$_9$ or a radical of formula IV, $R_5$ is hydrogen, $R_9$ is $C_1$–$C_4$alkyl, $R_{10}$ and $R_{11}$, together with the carbon atom to which they are bonded, form a cyclohexylidene ring, and p is 2.

11. A process according to claim 1, wherein the aqueous solvent is an aqueous alcohol.

12. A process for the preparation of compounds of formula I

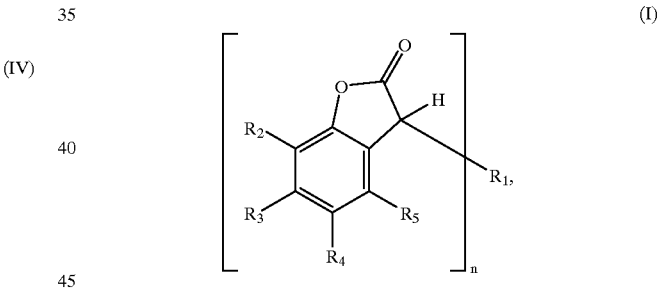

(I)

wherein the general symbols are as defined in claim 1, which process comprises converting a compound of formula VII

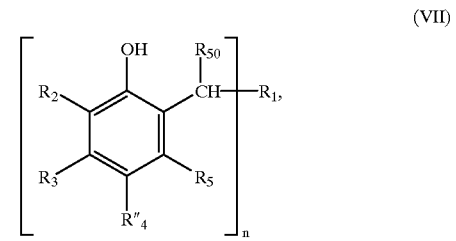

(VII)

wherein $R_1$ and n are as defined in claim 1, $R_2$, $R_3$, $R''_4$ and $R_5$ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R''_4$ or the radicals $R''_4$ and $R_5$, together with the carbon atoms to which they are bonded, form a benzo ring, $R''_4$ is additionally —$(CH_2)_p$—$COR_9$ or —$(CH_2)_q$OH or, when $R_3$ and $R_5$ are hydrogen, $R''_4$ is additionally a radical of formula VIII

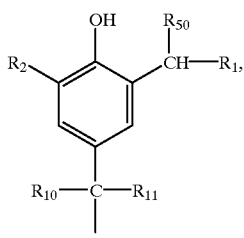
(VIII)

wherein $R_1$ is as defined in claim 1 for the case where n=1, $R_2$, $R_{10}$ and $R_{11}$ are as defined in claim 1,
$R_{50}$ is —$OR_{51}$, —$SR_{52}$,

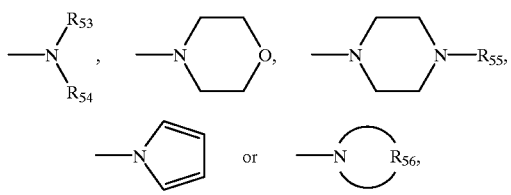

$R_{51}$ is $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$cycloalkyl; unsubstituted or $C_1$–$C_4$alkyl-substituted phenyl, $R_{52}$ is $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$cycloalkyl; unsubstituted or $C_1$–$C_4$alkyl-substituted phenyl, $R_{53}$ and $R_{54}$ are each independently of the other hydrogen, $C_1$–$C_{25}$ alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$-cycloalkyl; or a dendrimeric, oligomeric or polymeric $C_4$–$C_{100}$hydrocarbon radical, $R_{55}$ is $C_1$–$C_{25}$alkyl; $C_2$–$C_{25}$alkyl interrupted by oxygen or by sulfur; $C_7$–$C_9$phenylalkyl, unsubstituted or $C_1$–$C_4$alkyl-substituted $C_5$–$C_8$cycloalkyl; unsubstituted or $C_1$–$C_4$alkyl-substituted phenyl; or a radical of formula IX

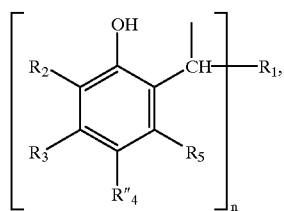
(IX)

wherein $R_1$ and n are as defined in claim 1,
$R_{56}$ is unsubstituted or $C_1$–$C_4$alkyl-substituted $C_2$–$C_{12}$alkylene,
with an aqueous cyanide salt solution to form a compound of formula V

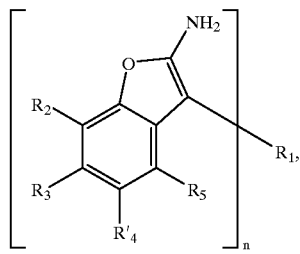
(V)

wherein the general symbols are as defined in claim 1, and then hydrolyzing the compound of formula V in an aqueous solvent in the presence of an acid.

13. A process according to claim 12, wherein $R_{50}$ is —$OR_{51}$, —$SR_{52}$,

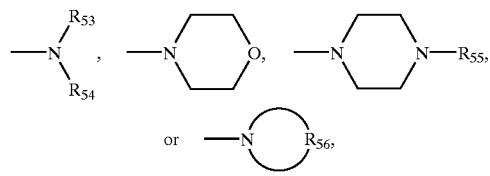

$R_{51}$ is $C_1$–$C_{12}$alkyl; $C_2$–$C_{12}$alkyl interrupted by oxygen; benzyl, $C_5$–$C_8$cycloalkyl or phenyl,
$R_{52}$ is $C_1$–$C_{12}$alkyl; $C_2$–$C_{12}$alkyl interrupted by oxygen; benzyl, $C_5$–$C_8$cycloalkyl or phenyl,
$R_{53}$ and $R_{54}$ are each independently of the other hydrogen, $C_1$–$C_{12}$alkyl; $C_2$–$C_{12}$alkyl interrupted by oxygen; benzyl, $C_5$–$C_8$cycloalkyl, or a dendrimeric or oligomeric or polymeric $C_4$–$C_{50}$hydrocarbon radical,
$R_{55}$ is $C_1$–$C_{12}$alkyl; $C_2$–$C_{12}$alkyl interrupted by oxygen; benzyl, $C_5$–$C_8$cycloalkyl, phenyl or a radical of formula IX

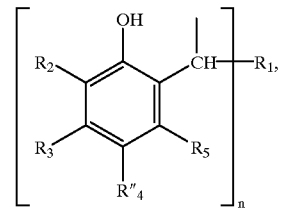
(IX)

wherein $R_1$ and n are as defined in claim 12, and
$R_{56}$ is $C_2$–$C_8$alkylene.

14. A process according to claim 12, wherein $R_{50}$ is

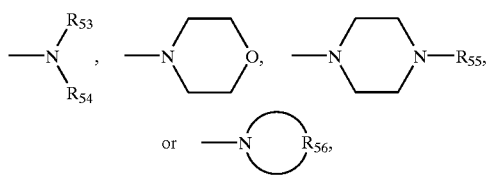

$R_{53}$ and $R_{54}$ are each independently of the other hydrogen, $C_1$–$C_{12}$alkyl, benzyl, cyclohexyl or a dendrimeric $C_4$–$C_{30}$hydrocarbon radical, $R_{55}$ is $C_1$–$C_{12}$alkyl, benzyl, cyclohexyl, phenyl or a radical of formula IX

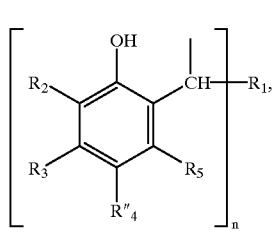

(IX)

wherein $R_1$ and n are as defined in claim 12, and
$R_{56}$ is $C_4$–$C_8$alkylene.

15. A process according to claim 12, wherein $R_{50}$ is

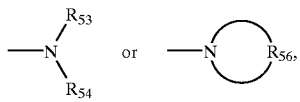

$R_{53}$ and $R_{54}$ are each independently of the other $C_1$–$C_{12}$alkyl, benzyl or a dendrimeric $C_4$–$C_{30}$hydrocarbon radical, and
$R_{56}$ is $C_4$–$C_6$alkylene.

16. A process according to claim 12, wherein the cyanide salt is an alkali metal cyanide salt.

17. A compound of formula V

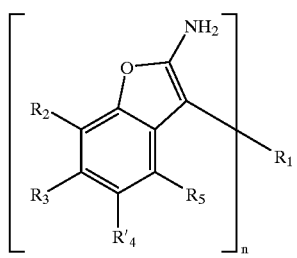

(V)

wherein, when n is 1,
$R_1$ is naphthyl, phenanthryl, anthryl, 5,6,7,8-tetrahydro-2-naphthyl, thienyl, benzo[b]thienyl, naphtho[2,3-b]thienyl, thianthrenyl, furyl, benzofuryl, isobenzofuryl, dibenzofuryl, xanthenyl, phenoxathiinyl, pyrrolyl, imidazolyl, pyrazolyl, pyrazinyl, pyridyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, biphenyl, terphenyl, fluorenyl or phenoxazinyl, each of which is unsubstituted or substituted by fluorine, hydroxy, $C_1$–$C_{18}$alkyl, $C_1$–$C_{18}$alkoxy, $C_1$–$C_{18}$alkylthio, di-($C_1$–$C_4$alkyl)amino, phenyl, benzyl, benzoyl or by benzoyloxy or $R_1$ is a radical of formula II or III

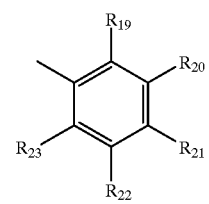

(II)

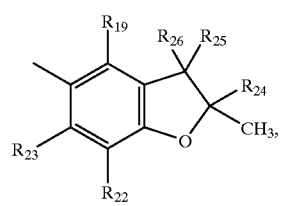

(III)

when n is 2,
$R_1$ is phenylene or naphthylene each unsubstituted or substituted by $C_1$–$C_4$alkyl or by fluorine; or is —$R_6$—X—$R_7$—,
$R_2$, $R_3$, $R'_4$ and $R_5$ are each independently of the others hydrogen, fluorine, hydroxy, $C_1$–$C_{25}$-alkyl, $C_7$–$C_9$phenylalkyl, unsubstituted or $C_1$–$C_4$alkyl-substituted phenyl, unsubstituted or $C_1$–$C_4$alkyl-substituted $C_5$–$C_8$cycloalkyl; $C_1$–$C_{18}$alkoxy, $C_1$–$C_{18}$alkylthio, $C_1$–$C_4$alkylamino, di-($C_1$–$C_4$alkyl)amino, $C_1$–$C_{25}$alkanoyloxy, $C_1$–$C_{25}$alkanoylamino; $C_3$–$C_{25}$alkanoyloxy interrupted by oxygen, sulfur or by

$C_6$–$C_9$cycloalkylcarbonyloxy, benzoyloxy or $C_1$–$C_{12}$alkyl-substituted benzoyloxy, or furthermore the radicals $R_2$ and $R_3$ or the radicals $R_3$ and $R'_4$ or the radicals $R'_4$ and $R_5$, together with the carbon atoms to which they are bonded, form a benzo ring, $R'_4$ is additionally —(CH$_2$)$_p$—COR$_9$ or —(CH$_2$)$_q$OH or, when $R_3$ and $R_5$ are hydrogen, $R'_4$ is additionally a radical of formula VI

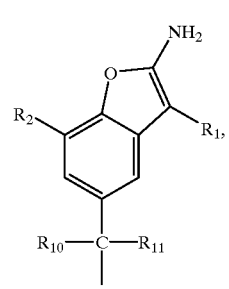

(VI)

wherein $R_1$ is as defined above for the case where n=1, $R_6$ and $R_7$ are each independently of the other phenylene or naphthylene each unsubstituted or substituted by $C_1$–$C_4$alkyl, $R_8$ is $C_1$–$C_8$alkyl, $R_9$ is hydroxy, $$\left[-O^-\frac{1}{r}M^{r+}\right],$$

$C_1$–$C_{18}$alkoxy or

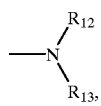

$R_{10}$ and $R_{11}$ are each independently of the other hydrogen, $CF_3$, $C_1$–$C_{12}$alkyl or phenyl, or $R_{10}$ and $R_{11}$ together with the carbon atom to which they are bonded, form a $C_5$–$C_8$cycloalkylidene ring unsubstituted or substituted by from 1 to 3 $C_1$–$C_4$alkyl groups;

$R_{12}$ and $R_{13}$ are each independently of the other hydrogen or $C_1$–$C_{18}$alkyl, $R_{14}$ is hydrogen or $C_1$–$C_{18}$alkyl, $R_{19}$, $R_{20}$, $R_{21}$, $R_{22}$ and $R_{23}$ are each independently of the others hydrogen, halogen, fluoro-substituted $C_1$–$C_{12}$alkyl; —CN,

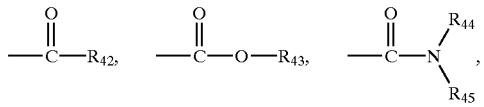

—$SOR_{46}$, —$SO_2R_{46}$, $SO_3R_{46}$, hydroxy, $C_1$–$C_{25}$alkyl; $C_2$–$C_{25}$alkyl interrupted by oxygen, sulfur or by

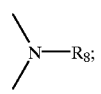

$C_1$–$C_{25}$alkoxy; $C_2$–$C_{25}$alkoxy interrupted by oxygen, sulfur or by

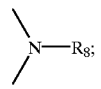

$C_1$–$C_{25}$alkylthio, $C_7$–$C_9$phenylalkyl, $C_7$–$C_9$phenylalkoxy, unsubstituted or $C_1$–$C_4$alkyl-substituted phenyl; unsubstituted or $C_1$–$C_4$alkyl-substituted phenoxy; unsubstituted or $C_1$–$C_4$alkyl-substituted $C_5$–$C_8$cycloalkyl; unsubstituted or $C_1$–$C_4$alkyl-substituted $C_5$–$C_8$cycloalkoxy;

di($C_1$–$C_4$alkyl)amino, $C_1$–$C_{25}$alkanoyl; $C_3$–$C_{25}$alkanoyl interrupted by oxygen, sulfur or by

$C_1$–$C_{25}$alkanoyloxy; $C_3$–$C_{25}$alkanoyloxy interrupted by oxygen, sulfur or by

$C_1$–$C_{25}$alkanoylamino, $C_6$–$C_9$cycloalkylcarbonyl, $C_6$–$C_9$cycloalkylcarbonyloxy, benzoyl or $C_1$–$C_{12}$alkyl-substituted benzoyl; benzoyloxy or $C_1$–$C_{12}$alkyl-substituted benzoyloxy;

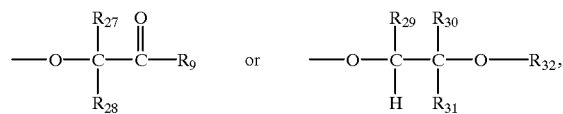

$R_{24}$ is hydrogen, $C_1$–$C_4$alkyl, or unsubstituted or $C_1$–$C_4$alkyl-substituted phenyl, $R_{25}$ and $R_{26}$ are hydrogen, $C_1$–$C_4$alkyl or phenyl, with the proviso that at least one of the radicals $R_{25}$ and $R_{26}$ is hydrogen, $R_{27}$ and $R_{28}$ are each independently of the other hydrogen, $C_1$–$C_4$alkyl or phenyl, $R_{29}$ is hydrogen or $C_1$–$C_4$alkyl, $R_{30}$ is hydrogen, unsubstituted or $C_1$–$C_4$alkyl-substituted phenyl; $C_1$–$C_{25}$alkyl; $C_2$–$C_{25}$alkyl interrupted by oxygen, sulfur or by

$C_7$–$C_9$phenylalkyl unsubstituted or substituted on the phenyl radical by from 1 to 3 $C_1$–$C_4$alkyl groups; or $C_7$–$C_{25}$phenylalkyl interrupted by oxygen, sulfur or by

and unsubstituted or substituted on the phenyl radical by from 1 to 3 $C_1$–$C_4$alkyl groups, $R_{31}$ is hydrogen or $C_1$–$C_4$alkyl, $R_{32}$ is hydrogen, $C_1$–$C_{25}$alkanoyl; $C_3$–$C_{25}$alkanoyl interrupted by oxygen, sulfur or by

$C_2$–$C_{25}$alkanoyl substituted by a di($C_1$–$C_6$alkyl) phosphonate group; $C_6$–$C_9$cycloalkylcarbonyl, thenoyl, furoyl, benzoyl, or $C_1$–$C_{12}$alkyl-substituted benzoyl;

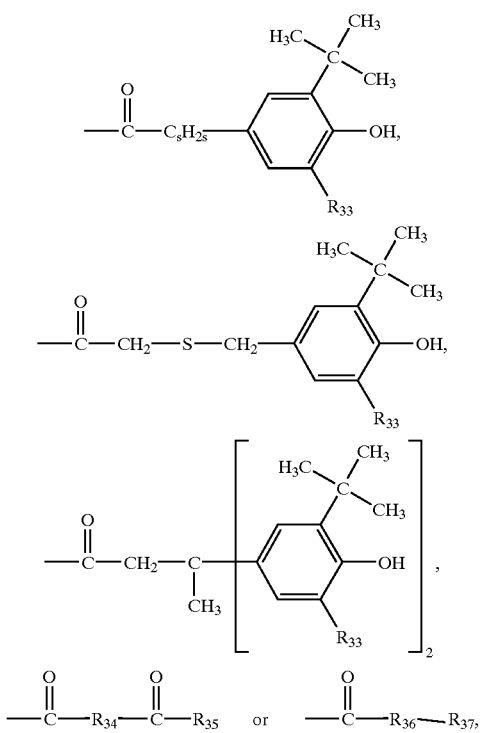

$R_{33}$ is hydrogen or $C_1$–$C_8$alkyl, $R_{34}$ is a direct bond, $C_1$–$C_{18}$alkylene; $C_2$–$C_{18}$alkylene interrupted by oxygen, sulfur or by

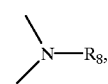

$C_2$–$C_{20}$alkylidene, $C_7$–$C_{20}$phenylalkylidene, $C_5$–$C_8$cycloalkylene, $C_7$–$C_8$bicycloalkylene, unsubstituted or $C_1$–$C_4$alkyl-substituted phenylene,

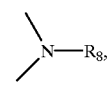

$R_{35}$ is hydroxy, $$\left[ -O^- \frac{1}{r} M^{r+} \right],$$

$C_1$–$C_{18}$alkoxy or

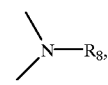

$R_{36}$ is oxygen, —NH— or

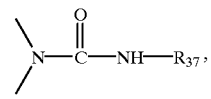

$R_{37}$ is $C_1$–$C_{18}$alkyl or phenyl, $R_{42}$ is hydrogen, hydroxy, $$\left[ -O^- \frac{1}{r} M^{r+} \right],$$

$C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

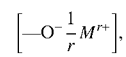

$R_{43}$ is $C_1$–$C_{25}$alkyl, $C_7$–$C_9$phenylalkyl, unsubstituted or $C_1$–$C_4$alkyl-substituted phenyl; unsubstituted or $C_1$–$C_4$alkyl-substituted $C_5$–$C_8$cycloalkyl; or $C_3$–$C_{25}$alkyl which is interrupted by oxygen, sulfur or

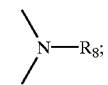

$R_{44}$ and $R_{45}$ are each independently of one another hydrogen, $C_1$–$C_{25}$alkyl, hydroxyl-substituted $C_2$–$C_{24}$alkyl; $C_3$–$C_{25}$alkyl which is interrupted by oxygen, sulfur or $C_7$–$C_9$-phenylalkyl which is unsubstituted or is substituted on the phenyl ring by $C_1$–$C_4$alkyl; or $C_3$–$C_{24}$alkenyl; or $R_{44}$ and $R_{45}$, together with the nitrogen atom to which they are attached, form a 5-, 6- or 7-membered heterocyclic ring which is unsubstituted or is substituted by $C_1$–$C_4$alkyl or is interrupted by oxygen, sulfur or $R_{46}$ is hydrogen or $C_1$–$C_{25}$alkyl,
M is an r-valent metal cation,
X is a direct bond, oxygen, sulfur or —$NR_{14}$—,
n is 1 or 2,
p is 0, 1 or 2,
q is 1,2,3,4,5 or 6,
r is 1, 2 or 3, and
s is 0, 1 or 2; with the proviso that, when $R_2$, $R_3$, $R_5$, $R_{19}$, $R_{20}$, $R_{21}$, $R_{22}$ and $R_{23}$ are hydrogen, $R'_4$ is not methylthio.

* * * * *